(12) United States Patent
Stender et al.

(10) Patent No.: US 9,537,095 B2
(45) Date of Patent: Jan. 3, 2017

(54) TELLURIUM COMPOUNDS USEFUL FOR DEPOSITION OF TELLURIUM CONTAINING MATERIALS

(71) Applicant: Entegris, Inc., Billerica, MA (US)

(72) Inventors: Matthias Stender, Phoenix, AZ (US); Chongying Xu, New Milford, CT (US); Tianniu Chen, Westford, MA (US); William Hunks, Waterbury, CT (US); Philip S. H. Chen, Bethel, CT (US); Jeffrey F. Roeder, Brookfield, CT (US); Thomas H. Baum, New Fairfield, CT (US)

(73) Assignee: Entegris, Inc., Billerica, MA (US)

( * ) Notice: Subject to any disclaimer, the term of this patent is extended or adjusted under 35 U.S.C. 154(b) by 50 days.

(21) Appl. No.: 14/332,924

(22) Filed: Jul. 16, 2014

(65) Prior Publication Data

US 2014/0329357 A1 Nov. 6, 2014

Related U.S. Application Data

(63) Continuation of application No. 13/911,622, filed on Jun. 6, 2013, now Pat. No. 8,796,068, which is a (Continued)

(51) Int. Cl.
*C23C 16/00* (2006.01)
*H01L 45/00* (2006.01)
(Continued)

(52) U.S. Cl.
CPC ......... *H01L 45/1616* (2013.01); *C07C 333/16* (2013.01); *C07C 395/00* (2013.01); *C07F 7/10* (2013.01); *C23C 16/305* (2013.01)

(58) Field of Classification Search
CPC ....... H01L 45/1616; C07C 33/16; C30B 25/02
(Continued)

(56) References Cited

U.S. PATENT DOCUMENTS 4,927,670 A 5/1990 Erbil
4,946,994 A 8/1990 Higa
(Continued)

FOREIGN PATENT DOCUMENTS

CN 1078574 A 11/1993
CN 1252885 A 5/2000
(Continued)

OTHER PUBLICATIONS

Foley, S., et al., "Synthesis and Characterization of Iron Complexes With Monoanionic and Dianionic N,N',N"-Trialkylguanidinate Ligands", "Inorg. Chem.", Jul. 12, 2002, pp. 4149-4157, vol. 41, No. 16.
(Continued)

*Primary Examiner* — Khanh Tuan Nguyen

(57) ABSTRACT

Precursors for use in depositing tellurium-containing films on substrates such as wafers or other microelectronic device substrates, as well as associated processes of making and using such precursors, and source packages of such precursors. The precursors are useful for deposition of $Ge_2Sb_2Te_5$ chalcogenide thin films in the manufacture of nonvolatile Phase Change Memory (PCM), by deposition techniques such as chemical vapor deposition (CVD) and atomic layer deposition (ALD).

20 Claims, 5 Drawing Sheets

Related U.S. Application Data continuation of application No. 12/392,009, filed on Feb. 24, 2009, now abandoned.

(60) Provisional application No. 61/030,980, filed on Feb. 24, 2008, provisional application No. 61/050,183, filed on May 2, 2008.

(51) Int. Cl.
  *C07C 333/16* (2006.01)
  *C07C 395/00* (2006.01)
  *C07F 7/10* (2006.01)
  *C23C 16/30* (2006.01)

(58) Field of Classification Search
  USPC .................. 427/248.1; 438/102; 117/101
  See application file for complete search history.

(56) References Cited

U.S. PATENT DOCUMENTS

| | | | |
|---|---|---|---|
| 4,948,623 A | 8/1990 | Beach et al. | |
| 4,960,916 A | 10/1990 | Pazik | |
| 4,962,214 A | 10/1990 | Villacorta et al. | |
| 4,975,299 A | 12/1990 | Mir et al. | |
| 5,091,570 A | 2/1992 | Mullin et al. | |
| 5,157,136 A | 10/1992 | Arnold et al. | |
| 5,166,428 A | 11/1992 | Cole-Hamilton et al. | |
| 5,296,716 A | 3/1994 | Ovshinsky et al. | |
| 5,312,983 A | 5/1994 | Brown et al. | |
| 5,359,205 A | 10/1994 | Ovshinsky | |
| 5,442,112 A | 8/1995 | Cole-Hamilton et al. | |
| 5,453,494 A | 9/1995 | Kirlin et al. | |
| 5,596,522 A | 1/1997 | Ovshinsky et al. | |
| 5,718,761 A * | 2/1998 | Tokunaga ............... C30B 25/02 117/101 | |
| 5,972,743 A | 10/1999 | Glassman et al. | |
| 6,005,127 A | 12/1999 | Todd et al. | |
| 6,086,779 A | 7/2000 | Bishop et al. | |
| 6,123,993 A | 9/2000 | Xu et al. | |
| 6,146,608 A | 11/2000 | Todd et al. | |
| 6,269,979 B1 | 8/2001 | Dumont | |
| 6,281,022 B1 | 8/2001 | Li et al. | |
| 6,331,211 B1 | 12/2001 | Xu et al. | |
| 6,511,718 B1 | 1/2003 | Paz de Araujo et al. | |
| 6,646,122 B1 | 11/2003 | Nuhlen et al. | |
| 6,699,637 B2 | 3/2004 | Ogawa et al. | |
| 6,750,079 B2 | 6/2004 | Lowrey et al. | |
| 6,787,186 B1 | 9/2004 | Hintermaier | |
| 6,861,559 B2 | 3/2005 | Odom | |
| 6,869,638 B2 | 3/2005 | Baum et al. | |
| 6,872,963 B2 | 3/2005 | Kostylev et al. | |
| 6,984,591 B1 | 1/2006 | Buchanan et al. | |
| 6,998,289 B2 | 2/2006 | Hudgens et al. | |
| 7,029,978 B2 | 4/2006 | Dodge | |
| 7,087,482 B2 | 8/2006 | Yeo et al. | |
| 7,115,927 B2 | 10/2006 | Hideki et al. | |
| 7,173,271 B2 | 2/2007 | Chang | |
| 7,312,165 B2 | 12/2007 | Jursich et al. | |
| 7,371,429 B2 | 5/2008 | Lee et al. | |
| 7,397,060 B2 | 7/2008 | Lung | |
| 7,399,666 B2 | 7/2008 | Ahn et al. | |
| 7,402,851 B2 | 7/2008 | Hideki et al. | |
| 7,419,698 B2 | 9/2008 | Jones | |
| 7,425,735 B2 | 9/2008 | Park et al. | |
| 7,462,900 B2 | 12/2008 | Hideki et al. | |
| 7,476,917 B2 | 1/2009 | Hideki et al. | |
| 7,488,967 B2 | 2/2009 | Burr et al. | |
| 7,518,007 B2 | 4/2009 | Seo et al. | |
| 7,569,417 B2 | 8/2009 | Lee et al. | |
| 7,615,401 B2 | 11/2009 | Park et al. | |
| 7,638,645 B2 | 12/2009 | Gordon et al. | |
| 7,638,787 B2 | 12/2009 | An et al. | |
| 7,666,789 B2 | 2/2010 | Choi et al. | |
| 7,667,218 B2 | 2/2010 | Yamamoto et al. | |
| 7,704,787 B2 | 4/2010 | Hideki et al. | |
| 7,727,884 B2 | 6/2010 | Bae et al. | |
| 7,728,172 B2 | 6/2010 | Lee et al. | |
| 7,737,290 B2 | 6/2010 | Gordon et al. | |
| 7,803,657 B2 | 9/2010 | Choi et al. | |
| 7,838,329 B2 | 11/2010 | Hunks et al. | |
| 7,858,152 B2 | 12/2010 | Ovshinsky et al. | |
| 7,902,048 B2 | 3/2011 | Shin et al. | |
| 7,935,564 B2 | 5/2011 | Breitwisch et al. | |
| 7,943,502 B2 | 5/2011 | Park et al. | |
| 7,943,923 B2 | 5/2011 | Gidon | |
| 7,960,205 B2 | 6/2011 | Xiao et al. | |
| 8,008,117 B2 | 8/2011 | Hunks et al. | |
| 8,093,140 B2 | 1/2012 | Chen et al. | |
| 8,268,665 B2 | 9/2012 | Hunks et al. | |
| 8,288,198 B2 | 10/2012 | Roeder et al. | |
| 8,709,863 B2 | 4/2014 | Hunks et al. | |
| 8,796,068 B2 | 8/2014 | Stender et al. | |
| 2002/0004266 A1 | 1/2002 | Hashimoto et al. | |
| 2002/0090815 A1 | 7/2002 | Koike et al. | |
| 2003/0135061 A1 | 7/2003 | Norman et al. | |
| 2004/0012009 A1 | 1/2004 | Casagrande et al. | |
| 2004/0038808 A1 | 2/2004 | Hampden-Smith et al. | |
| 2004/0197945 A1 | 10/2004 | Woelk et al. | |
| 2004/0215030 A1 | 10/2004 | Norman | |
| 2005/0002227 A1 | 1/2005 | Hideki et al. | |
| 2005/0029502 A1 | 2/2005 | Hudgens | |
| 2005/0082624 A1 | 4/2005 | Gousev et al. | |
| 2005/0208699 A1 | 9/2005 | Furkay et al. | |
| 2005/0267345 A1 | 12/2005 | Korgel et al. | |
| 2005/0283012 A1 | 12/2005 | Xu et al. | |
| 2005/0287747 A1 | 12/2005 | Chakravarti et al. | |
| 2006/0006449 A1 | 1/2006 | Jeong et al. | |
| 2006/0027451 A1 | 2/2006 | Park et al. | |
| 2006/0035462 A1 | 2/2006 | Millward | |
| 2006/0046521 A1 | 3/2006 | Vaartstra et al. | |
| 2006/0049447 A1 | 3/2006 | Lee et al. | |
| 2006/0094860 A1 | 5/2006 | Take | |
| 2006/0110930 A1 | 5/2006 | Senzaki | |
| 2006/0115595 A1 | 6/2006 | Shenai-Khatkhate et al. | |
| 2006/0138393 A1 | 6/2006 | Seo et al. | |
| 2006/0141155 A1 | 6/2006 | Gordon et al. | |
| 2006/0141710 A1 | 6/2006 | Yoon et al. | |
| 2006/0172067 A1 | 8/2006 | Ovshinsky et al. | |
| 2006/0172083 A1 | 8/2006 | Lee et al. | |
| 2006/0180811 A1 | 8/2006 | Lee et al. | |
| 2006/0249369 A1 | 11/2006 | Marangon et al. | |
| 2007/0048977 A1 | 3/2007 | Lee et al. | |
| 2007/0090336 A1 | 4/2007 | Asano et al. | |
| 2007/0121363 A1 | 5/2007 | Lung | |
| 2007/0154637 A1 | 7/2007 | Shenai-Khatkhate et al. | |
| 2007/0160760 A1 | 7/2007 | Shin et al. | |
| 2007/0246748 A1 | 10/2007 | Breitwisch et al. | |
| 2008/0003359 A1 | 1/2008 | Gordon et al. | |
| 2008/0035906 A1 | 2/2008 | Park et al. | |
| 2008/0035961 A1 | 2/2008 | Chen et al. | |
| 2008/0054244 A1 | 3/2008 | Lee et al. | |
| 2008/0078984 A1 | 4/2008 | Park et al. | |
| 2008/0118636 A1 | 5/2008 | Shin et al. | |
| 2008/0145702 A1 | 6/2008 | Shin et al. | |
| 2008/0210163 A1 | 9/2008 | Carlson et al. | |
| 2008/0210924 A1 | 9/2008 | Shin | |
| 2008/0254218 A1 | 10/2008 | Lei et al. | |
| 2008/0254232 A1 | 10/2008 | Gordon et al. | |
| 2008/0272355 A1 | 11/2008 | Cho et al. | |
| 2008/0286446 A1 | 11/2008 | Kamepalli et al. | |
| 2008/0290335 A1 | 11/2008 | Lin et al. | |
| 2009/0020738 A1 | 1/2009 | Happ et al. | |
| 2009/0032952 A1 | 2/2009 | Chen et al. | |
| 2009/0050869 A1 | 2/2009 | Kim et al. | |
| 2009/0074652 A1 | 3/2009 | Dussarrat | |
| 2009/0075420 A1 | 3/2009 | Bae et al. | |
| 2009/0087561 A1 | 4/2009 | Chen et al. | |
| 2009/0097305 A1 | 4/2009 | Bae et al. | |
| 2009/0101883 A1 | 4/2009 | Lai et al. | |
| 2009/0112009 A1 | 4/2009 | Chen et al. | |
| 2009/0124039 A1 | 5/2009 | Roeder et al. | |
| 2009/0142881 A1 | 6/2009 | Xiao et al. | |
| 2009/0162973 A1 | 6/2009 | Gatineau et al. | |

(56) References Cited

U.S. PATENT DOCUMENTS

| | | |
|---|---|---|
| 2009/0191330 A1 | 7/2009 | Xiao |
| 2009/0215225 A1 | 8/2009 | Stender et al. |
| 2009/0227066 A1 | 9/2009 | Joseph et al. |
| 2009/0275164 A1 | 11/2009 | Chen et al. |
| 2009/0280052 A1 | 11/2009 | Xiao et al. |
| 2009/0291208 A1 | 11/2009 | Gordon et al. |
| 2009/0298223 A1 | 12/2009 | Cheek et al. |
| 2009/0299084 A1 | 12/2009 | Okubo et al. |
| 2009/0305458 A1 | 12/2009 | Hunks et al. |
| 2009/0321733 A1 | 12/2009 | Gatineau et al. |
| 2010/0012917 A1 | 1/2010 | Takaura et al. |
| 2010/0018439 A1 | 1/2010 | Cameron et al. |
| 2010/0054029 A1 | 3/2010 | Happ et al. |
| 2010/0055831 A1 | 3/2010 | An et al. |
| 2010/0159637 A1 | 6/2010 | Lee et al. |
| 2010/0190341 A1 | 7/2010 | Park et al. |
| 2010/0270527 A1 | 10/2010 | Sawamura |
| 2010/0317150 A1 | 12/2010 | Hunks et al. |
| 2010/0320434 A1 | 12/2010 | Choi et al. |
| 2011/0001107 A1 | 1/2011 | Zheng |
| 2011/0060165 A1 | 3/2011 | Cameron et al. |
| 2011/0065252 A1 | 3/2011 | Nakamura |
| 2011/0111556 A1 | 5/2011 | Chen et al. |
| 2011/0124182 A1 | 5/2011 | Zheng |
| 2011/0180905 A1 | 7/2011 | Zheng et al. |
| 2011/0227021 A1 | 9/2011 | Schrott et al. |
| 2011/0260132 A1 | 10/2011 | Zheng et al. |
| 2011/0263100 A1 | 10/2011 | Hunks et al. |
| 2012/0108038 A1 | 5/2012 | Chen et al. |
| 2013/0005078 A1 | 1/2013 | Roeder et al. |
| 2013/0078475 A1 | 3/2013 | Zheng |
| 2014/0220733 A1 | 8/2014 | Hunks et al. |

FOREIGN PATENT DOCUMENTS

| | | |
|---|---|---|
| CN | 1253597 A | 5/2000 |
| CN | 1726303 A | 1/2006 |
| CN | 101040371 A | 9/2007 |
| DE | 102008026889 A1 | 2/2009 |
| EP | 1675194 A2 | 6/2006 |
| EP | 1806427 A2 | 7/2007 |
| EP | 1995236 A1 | 11/2008 |
| EP | 2067876 A2 | 6/2009 |
| EP | 2130942 A2 | 12/2009 |
| JP | 58-38296 A | 3/1983 |
| JP | 5-311423 A | 11/1993 |
| JP | 2001-67720 A | 3/2001 |
| JP | 2002-211924 A | 7/2002 |
| JP | 2002-220658 A | 8/2002 |
| JP | 2004-349684 A | 12/2004 |
| JP | 2006-511716 A | 4/2006 |
| JP | 2006-124262 A | 5/2006 |
| JP | 2006-182781 A | 7/2006 |
| JP | 2007-56369 A | 3/2007 |
| JP | 2008-131046 A | 6/2008 |
| JP | 2008-252088 A | 10/2008 |
| JP | 2009-149980 A | 7/2009 |
| JP | 2011-66135 A | 3/2011 |
| KR | 10-2004-0076225 A | 8/2004 |
| KR | 10-2005-0048891 A | 5/2005 |
| KR | 10-2005-0084997 A | 8/2005 |
| KR | 10-0585175 B1 | 5/2006 |
| KR | 10-2006-0091160 A | 8/2006 |
| KR | 10-2007-0025612 A | 3/2007 |
| KR | 10-2007-0105752 A | 10/2007 |
| KR | 10-2008-0052362 A | 6/2008 |
| KR | 10-2008-0080273 A | 9/2008 |
| KR | 10-2009-0008799 A | 1/2009 |
| KR | 10-2009-0029488 A | 3/2009 |
| KR | 10-2009-0036771 A | 4/2009 |
| KR | 10-2009-0045132 A | 5/2009 |
| KR | 10-2009-0054925 A | 6/2009 |
| KR | 10-1067969 B1 | 9/2011 |
| SU | 768457 A | 10/1980 |
| WO | 2004046417 A2 | 6/2004 |
| WO | 2005084231 A2 | 9/2005 |
| WO | 2006012052 A2 | 2/2006 |
| WO | 2006023501 A2 | 3/2006 |
| WO | 2006083481 A2 | 8/2006 |
| WO | 2007067604 A2 | 6/2007 |
| WO | 2007070218 A2 | 6/2007 |
| WO | 2007126690 A2 | 11/2007 |
| WO | 2007140813 A1 | 12/2007 |
| WO | 2008002546 A1 | 1/2008 |
| WO | 2008057616 A2 | 5/2008 |
| WO | 2009034775 A1 | 3/2009 |
| WO | 2009039187 A1 | 3/2009 |
| WO | 2009134989 A2 | 11/2009 |
| WO | 2010055423 A2 | 5/2010 |
| WO | 2010135702 A2 | 11/2010 |
| WO | 2011002705 A2 | 1/2011 |

OTHER PUBLICATIONS

Gantzel, P., et al., "Synthesis and Crystal Structures of Lithium and Potassium Triazenide Complexes", "Inorg. Chem.", Jun. 19, 1998, pp. 3450-3451, vol. 37, No. 14.

Gedridge, R., et al., "Syntheses and Mechanistic Studies of Symmetric Tetraorganyltellurium (IV) (R4Te) and Diorganyltellurium (II) (R'Te) Compounds (R=R'=Me, n-Bu, Me3SiCH2, and CH2=CH; R'=t-Bu and Allyl)", "Organometallics", 1991, pp. 286-291, vol. 10.

Green, S., et al., "Synthetic, structural and theoretical studies of amidinate and guanidinate stabilised germanium(I) dimers", "Chem. Commun.", Sep. 8, 2006, pp. 3978-3980.

Gumrukcu, I., et al., "Electron Spin Resonance of t-Alkyl-, Silyl-, and Germyl-aminyl Radicals and some Observations on the Amides MBr{N(SiMe3)2}3 (M=Ge,Sn, or Pb)", "J.C.S. Chem. Comm.", 1980, pp. 776-777.

Gupta, A., et al. , "Triorganoantimony(V) complexes with internally functionallized oximes: synthetic, spectroscopic and structural aspects of [R3Sb(Br)L], [R3Sb(OH)L] and [R3SbL2], crystal and molecular structures of [Me3Sb{ON=C (Me)C4H3O}2], [Me3Sb{ON=C(Me)C4H3S}2], 2-OC4H3C(Me)=NOH and 2-SC4H3C(Me)=NOH", "Journal of Organometallic Chemistry", 2002, pp. 118-126, vol. 645.

Gynane, M., et al., "Subvalent Group 4B Metal Alkyls and Amides. Part 5. The Synthesis and Physical Properties of Thermally Stable Amides of Germanium(II), Tin(II), and Lead(II)", "J. Chem. Soc., Dalton Transactions", 1977, pp. 2004-2009.

Han, L., et al., "Extremely Facile Oxidative Addition of Silyl, Germyl, and Stannyl Tellurides and Other Chalcogenides to Platinum(0) Complexes, X-ray Structure of trans-Pt(4-PhC6H4Te)(SiMe3)(PEt3)2", "J. Am. Chem. Soc.", 1997, pp. 8133-8134, vol. 119.

Harris, D., et al., "Monomeric, Volatile Bivalent Amides of Group IVB Elements, M(NR12)2 and M(NR1R2)2 (M=Ge, Sn, or Pb; R1=Me3Si, R2=Me3C)", "J.C.S. Chem. Comm.", 1974, pp. 895-896.

Herrmann, W., et al. , "Stable Cyclic Germanediyls ('Cyclogermylenes'): Synthesis, Structure, Metal Complexes, and Thermolyses", "Angew. Chem. Int. Ed. Engl.", 1992, pp. 1485-1488, vol. 31, No. 11.

Horii, H., et al., "A Novel Cell Technology Using N-Doped GESBTE Films for Phase Change RAM", "Symposium on VLSI Technology Digest of Technical Papers", Jun. 10-12, 2003, pp. 177-178.

Jones, R., et al., "The Preparation of DI-t-Butyl Ditelluride and DI-t-Butyl Telluride and the 125Te NMR and Moessbauer Spectra of Some Dialkyl Tellurides and Ditellurides", "Journal of Organometallic Chemistry", 1983, pp. 61-70, vol. 255.

Karsch, H., et al., "Bis(amidinate) Complexes of Silicon and Germanium", "Eur. J. Inorg. Chemistry", Apr. 1998, pp. 433-436, vol. 4.

Karsch, H., et al., "A New Method for the Generation of Silaheterocycles via [4+1]-Cycloaddition Reaction in the System Heterobutadiene/HSiCl3/NR3", "Z. anorg. allg. Chem.", Feb. 1998, pp. 295-309, vol. 624, No. 2.

(56) References Cited

OTHER PUBLICATIONS

Kilner, M., et al., "Studies of Amidino-Complexes of Copper(I) and (II). Carboxylate Analogues", "Polyhedron", Jan. 1983, pp. 1379-1388, vol. 2, No. 12.

Kim, R., et al., "Structural Properties of Ge2Sb2Te5 thin films by metal organic chemical vapor deposition for phase change memory applications", "Applied Physics Letters", Sep. 6, 2006, pp. 13, vol. 89, No. 102107.

Kim, S., et al., "Electrical Properties and Crystal Structures of Nitrogen-Doped Ge2Sb2Te5 Thin Film for Phase Change Memory", "Thin Solid Films", Dec. 22, 2004, pp. 322-326, vol. 469-470.

Kissounko, D., et al., "Principal trends in the chemistry of amidinate complexes of main-group and transition elements", "Russian Chemical Reviews", May 1, 2006, pp. 351-374, vol. 75, No. 5.

Kuehl, O., "N-heterocyclic germylenes and related compounds", "Coordination Chemistry Reviews", 2004, pp. 411-427, vol. 248.

Lappert, M., et al., "Monomeric Bivalent Group 4B Metal Dialkylamides M[NCMe2(CH2)3CMe2] (M=Ge or Sn), and the Structure of a Gaseous Disilylamide, Sn[N(SiMe3)2]2, by Gas Electron Diffraction", "J.C.S. Chem. Comm.", 1979, pp. 369-370, vol. 8.

Lappert, M., et al., "Monomeric, Coloured Germanium(II) and Tin(II) Di-t-Butylamides, and the Crystal and Molecular Structure of Ge(NCMe2[CH2]3CMe2)2", "J.C.S. Chem. Comm.", 1980, pp. 621-622, vol. 13.

Lee, J., et al., "GeSbTe deposition for the PRAM application", "Applied Surface Science", Feb. 2007, pp. 3969-3976, vol. 253, No. 8.

Lim, B., et al., "Synthesis and Characterization of Volatile, Thermally Stable, Reactive Transition Metal Amidinates", "Inorg. Chem.", Oct. 25, 2003, pp. 7951-7958, vol. 42, No. 24.

Littke, A., et al., "Bulky Bis(Alkylamidinate) Complexes of Group 4. Syntheses and Characterization of M(CYNC(R')NCY)2Cl2 and Zr(CYNC(ME)NCY)2ME2 (R'=ME, M-TI, Zr, HF; R'=TbU, M=Zr)", "Organometallics", Jan. 16, 1998, pp. 446-451, vol. 17, No. 3.

Lu, Z., et al., "Tetrasubstituted Guanidinate Anions and Supporting Ligands in Organoyttrium Chemistry", "Organometallics", Jan. 16, 2001, pp. 706-712, vol. 20, No. 4.

MaComber, D., et al., "(n5-Cyclopentadienyl)- and (n5-Pentamethylcyclopentadienyl)copper Compounds Containing Phosphine, Carbonyl, and n2-Acetylenic Ligands", "J. Am. Chem. Soc.", 1983, pp. 5325-5329, vol. 105.

Mathur, S., et al., "Germanium Nanowires and Core-Shell Nanostructures by Chemical Vapor Deposition of [Ge (C5H5)2]", "Chem. Mater.", May 15, 2004, pp. 2449-2456, vol. 16, No. 12.

Meller, A., et al., "Synthesis and Isolation of New Germanium(II) Compounds and of Free Germylenes", "Chem. Ber.", May 1985, pp. 2020-2029 (English Abstract), vol. 118, No. 5.

Milanov, A., et al., "Bis(2-butyl-N, N'-diisopropylamidinato) dichlorohafnium(IV)", "Acta Crystallographica. Section C: Crystal Structure Communications", Jun. 30, 2005, pp. m370-m372, vol. 61, No. 7.

Oakley, S., et al., "Structural consequences of the prohibition of hydrogen bonding in copper-guanidine systems", "Inorg. Chem.", Jul. 13, 2004, pp. 5168-5172, vol. 43, No. 16 (Abstract).

Oszczapowicz, J., "12. Basicity, H-bonding and complex formation (Edited by Patai, S., et al.)", "The chemistry of amidines and imidines", 1991, pp. 677-681, vol. 2, Publisher: John Wiley & Sons, Published in: Chichester.

Raj, P., et al. , "Synthesis and characterization of the complex triorganoantimony (V) cations, R3SbL'2+ and R3Sb (L-L)2+", "Synthesis and Reactivity in Inorganic and Metal-Organic Chemistry", 1992, pp. 543-557 (Abstract), vol. 22, No. 5.

Raj, P., et al. , "Synthesis and geometry of complex triorganoantimony(V) cations", "Synthesis and Reactivity in Inorganic and Metal-Organic Chemistry", 1992, pp. 1471-1494 (Abstract), vol. 22, No. 10.

Ramos, J., et al., "Ab initio study of ethylene insertion into MC bonds of alkylamidinates complexes of group IV ({R'NCRNR'}2MCH3+, M=Zr, Ti, R=H, Ph and R=H, SiMe3)", "Polymer", May 11, 2001, p. 7278 vol. 42, No. 17.

Ren, H., et al., "Synthesis and structures of cyclopentadienyl N-heterocyclic carbene copper(I) complexes", "Journal of Organometallic Chemistry", Jun. 21, 2006, pp. 4109-4113, vol. 691.

Sadique, A., et al., "Monomeric and Dimeric Amidinate Complexes of Magnesium", "Inorg. Chem.", Nov. 26, 2001, pp. 6349-6355, vol. 40, No. 25.

Schoeller, W., et al., "Bonding Properties of Amidinate Compexes of the Group 14 Elements Silicon, Germanium, Tin and Lead in Their Divalent and Tetravalent Oxidation States", "Inorg., Chem.", Dec. 17, 1998, pp. 29-37, vol. 38, No. 1.

Shi, Y., et al., "Titanium dipyrrolylmethane derivatives: rapid intermolecular alkyne hydroamination", "Chem. Comm.", Mar. 7, 2003, pp. 586-587, No. 5.

Stauf, G., et al., "Low Temperature ALD of Germanium for Phase Change Memory Thin Films", "AVS 7th International Conference on Atomic Layer Deposition—ALD 2007", Jun. 24, 2007, pp. 1-8.

Thiede, T., et al., "Evaluation of Homoleptic Guanidinate and Amidinate Complexes of Gadolinium and Dysprosium for MOCVD of Rare-Earth Nitride Thin Films", "Chem. Mater.", Feb. 24, 2011, pp. 1430-1440, (Abstract), vol. 23, No. 6.

Tin, M., et al. , "Insertion Routes to Tetrasubstituted Guanidinate Complexes of Ta(V) and Nb(V)", "Inorganic Chemistry", Feb. 18, 1999, pp. 998-1001, vol. 38, No. 5.

Tsumuraya, T., et al., "Telluradigermiranes. A Novel Three-membered Ring System Containing Tellurium", "J. Chem. Soc. Chem. Commun.", 1990, pp. 1159-1160.

Van Vliet, P., et al., "Complexes of N,N'-substituted formamidines I. Compounds [M(RNC(H)NR')]n (M=CuI, AgI; R=p-Tolyl; R'=Alkyl;N=2,4); and Study of the Dimer-Dimer and Dimer-Tetramer Equilibria in Solution", "J. Organo. Chem.", Oct. 9, 1979, pp. 89-100, vol. 179, No. 1.

Van Vliet, P., et al., "Metal-Metal Bonded Compounds. VI. Rhodium-Mercury Bonded Complexes [(DIENE){RNC(Y)NR'}2RHGCL]2 Containing Interchanging Metal-Metal Bridging and Chelating Amidino Groups", "Journal of Organometallic Chemistry", 1980, pp. 301-310, vol. 188.

Van Vliet, P., et al., "Metal-Metal Bonded Compounds. IV. Stabilization of Metal-Metal Bonding by Bridging Asymmetric Formamidino Ligands in Complexes [(PH3P)2(Co)IRM(RNC(H)NR')Cl] (M=Cu, Ag; R=Alkyl; R'=P-Tolyl)", "Journal of Organometallic Chemistry", 1979, pp. 105-115, vol. 182.

Veprek, S., et al., "Organometallic chemical vapor deposition of germanium from a cyclic germylene, 1,3-Di-tert-butyl-1,3,2-diazagermolidin-2-ylidine", "Chem. Mater.", 1996, pp. 825-831, vol. 8.

Willcocks, A., et al., "Multinuclear Copper(I) Guanidinate Complexes", "Inorganic Chemistry", Dec. 14, 2011, pp. 246-257, vol. 51.

Zhou, Y., et al., "Synthesis and Structure of Novel Bridged Dinuclear Indium Complexes", "Inorg. Chem.", Mar. 13, 1996, pp. 1423-1424, vol. 35, No. 6.

Zhou, Y., et al., "Bulky Amidinate Complexes of Tin(IV). Synthesis and Structure of Sn(RnC(R') NR)2Cl2 (R=Cyclohexyl, R'=H, ME; R=SiME3, R'=TbU)", "Inorg. Chem.", Feb. 12, 1997, pp. 501-504, vol. 36, No. 4.

Abrutis, A., et al., "Hot-Wire Chemical Vapor Deposition of Chalcogenide Materials for Phase Change Memory Applications", "Chem. Mater.", May 2008, pp. 3557-3559, vol. 20, No. 11.

Aeilts, S., et al., "Aluminum Alkyl Complexes Containing Guanidinate Ligands", "Organometallics", Jun. 24, 1998, pp. 3265-3270, vol. 17.

Aharonovich, S., et al., "N,N'-Bis-Silylated Lithium Aryl Amidinates: Synthesis, Characterization, and the Gradual Transition of Coordination Mode From Omega Toward Pi Originated by Crystal Packing Interactions", "Organometallics", Mar. 15, 2008, pp. 1869-1877, vol. 27.

Anderson, H., "Dialkylaminogermanes and Dialkylaminosilanes", "J. Amer. Chem. Soc.", Mar. 20, 1952, pp. 1421-1423, vol. 74, No. 6.

(56) References Cited

OTHER PUBLICATIONS

Anderson, Q., et al., "Synthesis and Characterization of the First Pentaphenylcyclopentadienyl Copper(I) Complex, (Ph5Cp)Cu(PPh3)", "Organometallics", 1998, pp. 4917-4920, vol. 17.

Archibald, S., et al., "Synthesis and Characterization of Silver(I) Complexes With C-Alkyl Functionalized N,N'-Diphenylamidinates: Tetrameric and Trimeric Structural Motifs", "Journal of Cluster Science", Mar. 2000, pp. 261-283 (Abstract Only), vol. 11, No. 1.

Artaud-Gillet, M., et al., "Evaluation of copper organometallic sources for CuGaSe2 photovoltaic applications", "Journal of Crystal Growth", 2003, pp. 163-168, vol. 248.

Auner, N., et al., "Organosilicon Chemistry IV: From Molecules to Materials", Mar. 2000, p. 291 (Abstract), Publisher: Wiley-Vch.

Baines, K., et al., "A Facile Digermene-to-germylgermylene Rearrangement; Bulky Germylene Insertion into the Si—H Bond", "J. Chem. Soc. Chem. Commun.", 1992, pp. 1484-1485.

Bazinet, P., et al., "Synthesis and Structural Investigation of N,N',N"-Trialkylguanidinato-Supported Zirconium(IV) Complexes", "Inorg. Chem.", Sep. 4, 2003, pp. 6225-6229, vol. 42.

Berno, P., et al., "Dinitrogen Fixation Versus Metal-Metal Bond Formation in the Chemistry of Vanadium(II) Amidinates", "J. Am. Chem. Soc.", Aug. 1994, pp. 7417-7418, vol. 116, No. 16.

Brinckman, F., et al., "Metal-Nitrogen Bonding. Covalent Complexes of 1,3-Dimethyltriazene With Elements of GROUPS I,II-,III,IV, and V1", "Inorganic Chemistry", Jul. 1965, pp. 936-942, vol. 4, No. 7.

Brown, I., et al., "The Crystal Structure of Diazoaminobenzene Copper (I)", "Acta Crystallographica", May 1961, pp. 480-485, vol. 14, No. 5.

Cheng, H., et al., "Wet Etching of Ge2Sb2Te5 Films and Switching Properties of Resultant Phase Change Memory Cells", "Semiconductor Science and Technology", Sep. 26, 2005, pp. 1111-1115, vol. 20, No. 11.

Chorley, R., et al., "Subvalent Group 14 metal compounds XIV. The X-ray crystal structures of two monomeric Group 14 metal bisamides, Ge[N(SiMe3)2]2 and Sn[NC(Me)2(CH2)3CMe2]2", "Inorganica Chimica Acta", Aug.-Oct. 1992, pp. 203-209, vol. 198-200.

Coles, M., et al., "Cationic Aluminum Alkyl Complexes Incorporating Amidinate Ligands. Transition-Metal-Free Ethylene Polymerization Catalysts", "J. Am. Chem. Soc.", Aug. 1997, pp. 8125-8126, vol. 119, No. 34.

Coles, M., et al., "Synthesis and Structures of Mono- and Bis(Amidinate) Complexes of Aluminum", "Organometallics", Nov. 25, 1997, pp. 5183-5194, vol. 16, No. 24.

Cummins, C., et al., "Synthesis of Terminal Vanadium(V) Imido, Oxo, Sulfido, Selenido, and Tellurido Complexes by Imido Group or or Chalcogen Atom Transfer to Trigonal Monopyramidal V[N3N] (N3N=[(Me3SiNCH2CH2)3N]3-", "Inorganic Chemistry", Mar. 30, 1994, pp. 1448-1457, vol. 33, No. 7.

Dagorne, S., et al., "Sterically Crowded Gallium Amidinate Complexes", "Organometallics", Oct. 7, 1999, pp. 4619-4623, vol. 18, No. 22.

Dawson, D., et al., "Organotantalum Bis(Amidinate) Complexes: Synthesis and Characterization of Methyl, Methylidene, Benzyl, and Imido Derivatives", "Organometallics", Mar. 18, 1997, pp. 1111-1113, vol. 16, No. 6.

Foley, S., et al., "Facile Formation of Rare Terminal Chalcogenido Germanium Complexes with Alkylamidinates as Supporting Ligands", "J. Am. Chem. Soc.", Oct. 29, 1997, pp. 10359-10363, vol. 119, No. 43.

Zhou, Y., et al., "N-Substituted Guanidinate Anions As Ancillary Ligands in Organolanthanide Chemistry. Synthesis and Characterization of {CYNC[N(SiMe3)2]NCY}2SmCH(SiMe3)2", "Organometallics", Sep. 4, 1998, pp. 4387-4391, vol. 17, No. 20.

* cited by examiner

TELLURIUM COMPOUNDS USEFUL FOR DEPOSITION OF TELLURIUM CONTAINING MATERIALS

CROSS-REFERENCE TO RELATED APPLICATIONS

This application is a continuation under 35 U.S.C. §120 of U.S. patent application Ser. No. 13/911,622, filed Jun. 6, 2013, which is a continuation under 35 U.S.C. §120 of U.S. patent application Ser. No. 12/392,009, filed on Feb. 24, 2009, which claims the benefit under 35 U.S.C. §119 of U.S. Provisional Patent Application No. 61/030,980 filed on Feb. 24, 2008 and U.S. Provisional Patent Application No. 61/050,183 filed on May 2, 2008. The disclosures of U.S. patent application Ser. No. 13/911,622, U.S. patent application Ser. No. 12/392,009, U.S. Provisional Patent Application No. 61/030,980 and U.S. Provisional Patent Application No. 61/050,183 are hereby incorporated herein by reference in their respective entireties, for all purposes.

FIELD OF THE INVENTION

The present invention relates to precursors for use in depositing tellurium-containing films on substrates such as wafers or other microelectronic device substrates, as well as associated processes of making and using such precursors, and source packages of such precursors.

DESCRIPTION OF THE RELATED ART

In the manufacture of microelectronic devices, there is emerging interest in the deposition of $Ge_2Sb_2Te_5$ chalcogenide thin films for nonvolatile Phase Change Memory (PCM), due to its relatively easy integration pathways with silicon-based integrated circuits. Chemical vapor deposition (CVD) and atomic layer deposition (ALD) processing of these materials are of primary interest as deposition techniques for advanced device applications.

The anticipated use of high aspect ratio geometries in PCMs and the corresponding requirement to achieve smooth films of proper phase and non-segregated character, require processes that are efficient in forming high-quality tellurium-containing films at low temperatures (<400° C.). Suitable tellurium precursors are required that are compatible with such requirements, and that preferably have high volatility, and are liquids at standard temperature and pressure conditions.

SUMMARY OF THE INVENTION

The present invention relates to tellurium precursors useful for depositing tellurium-containing films on substrates such as wafers or other microelectronic device substrates, as well as associated processes of making and using such precursors, and source packages of such precursors.

In one aspect, the invention relates to a tellurium precursor selected from among:
(i) Te(IV) organyls having the formula $TeR^1R^2R^3R^4$ wherein each of $R^1$, $R^2$, $R^3$ and $R^4$ is the same as or different from others, and each is independently selected from H, halogen, $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl and acetylalkyl;
(ii) tellurium bis-amides of the formula $Te[NR_2]_2$ wherein each R is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl;
(iii) asymmetric tellurium compounds including one alkyl substituent and a second ligand containing a heteroatom;
(iv) tellurium compounds with ethylenediamine ligands;
(v) tellurium compounds with dithiocarbamate ligands;
(vi) Te(II) and Te(IV) compounds including at least one nitrogen-based ligand selected from among amidinates, guanidinates, isoureates and beta-diketoiminates; and
(vii) dialkyl ditellurides wherein alkyl is $C_1$-$C_8$ alkyl.

In another aspect, the invention relates to a compound of the formula

$$XTeNR^1R^2$$

wherein
X is halogen; and
each of $R^1$ and $R^2$ is the same as or different from the other, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl.

In a further aspect, the invention relates to a composition comprising:
(a) a tellurium precursor selected from among:
(i) Te(IV) organyls having the formula $TeR^1R^2R^3R^4$ wherein each of $R^1$, $R^2$, $R^3$ and $R^4$ is the same as or different from others, and each is independently selected from H, halogen, $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl and acetylalkyl;
(ii) tellurium bis-amides of the formula $Te[NR_2]_2$ wherein each R is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl;
(iii) asymmetric tellurium compounds including one alkyl substituent and a second ligand containing a heteroatom;
(iv) tellurium compounds with ethylenediamine ligands;
(v) tellurium compounds with dithiocarbamate ligands;
(vi) Te(II) and Te(IV) compounds including at least one nitrogen-based ligand selected from among amidinates, guanidinates, isoureates and beta-diketoiminates; and
(vii) dialkyl ditellurides wherein alkyl is $C_1$-$C_8$ alkyl; and
(b) a solvent medium in which said compound is dissolved.

A further aspect of the invention relates to a composition comprising
(a) a compound of the formula:

$$ITeNR^1R^2$$

wherein
each of $R^1$ and $R^2$ is the same as or different from the other, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl; and
(b) a solvent medium in which said compound is dissolved.

A still further aspect of the invention relates to a precursor vapor comprising vapor of a tellurium precursor selected from the group consisting of
(i) Te(IV) organyls having the formula $TeR^1R^2R^3R^4$ wherein each of $R^1$, $R^2$, $R^3$ and $R^4$ is the same as or different from others, and each is independently selected from H, halogen, $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl and acetylalkyl;

(ii) tellurium bis-amides of the formula $Te[NR_2]_2$ wherein each R is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl;
(iii) asymmetric tellurium compounds including one alkyl substituent and a second ligand containing a heteroatom;
(iv) tellurium compounds with ethylenediamine ligands;
(v) tellurium compounds with dithiocarbamate ligands;
(vi) Te(II) and Te(IV) compounds including at least one nitrogen-based ligand selected from among amidinates, guanidinates, isoureates and beta-diketoiminates; and
(vii) dialkyl ditellurides wherein alkyl is $C_1$-$C_8$ alkyl.

Another aspect of the invention relates to a method of depositing a tellurium-containing film on a substrate, comprising volatilizing a tellurium precursor to form a precursor vapor, and contacting the substrate with the precursor vapor under deposition conditions to form the tellurium-containing film on the substrate, wherein said tellurium precursor is selected from the group consisting of:
(i) Te(IV) organyls having the formula $TeR^1R^2R^3R^4$ wherein each of $R^1$, $R^2$, $R^3$ and $R^4$ is the same as or different from others, and each is independently selected from H, halogen, $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl and acetylalkyl;
(ii) tellurium bis-amides of the formula $Te[NR_2]_2$ wherein each R is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl;
(iii) asymmetric tellurium compounds including one alkyl substituent and a second ligand containing a heteroatom;
(iv) tellurium compounds with ethylenediamine ligands;
(v) tellurium compounds with dithiocarbamate ligands;
(vi) Te(II) and Te(IV) compounds including at least one nitrogen-based ligand selected from among amidinates, guanidinates, isoureates and beta-diketoiminates; and
(vii) dialkyl ditellurides wherein alkyl is $C_1$-$C_8$ alkyl.

A further aspect of the invention relates to a packaged precursor, comprising a precursor storage and vapor dispensing vessel having disposed therein a tellurium precursor selected from among:
(i) Te(IV) organyls having the formula $TeR^1R^2R^3R^4$ wherein each of $R^1$, $R^2$, $R^3$ and $R^4$ is the same as or different from others, and each is independently selected from H, halogen, $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl and acetylalkyl;
(ii) tellurium bis-amides of the formula $Te[NR_2]_2$ wherein each R is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl;
(iii) asymmetric tellurium compounds including one alkyl substituent and a second ligand containing a heteroatom;
(iv) tellurium compounds with ethylenediamine ligands;
(v) tellurium compounds with dithiocarbamate ligands;
(vi) Te(II) and Te(IV) compounds including at least one nitrogen-based ligand selected from among amidinates, guanidinates, isoureates and beta-diketoiminates; and
(vii) dialkyl ditellurides wherein alkyl is $C_1$-$C_8$ alkyl Yet another aspect of the invention relates to a method for the preparation of a tellurium dialkylamide compound, comprising reacting tellurium dihalide with a metal amide to yield said tellurium dialkylamide compound.

A further aspect of the invention relates to a method of forming a GST film on a substrate, comprising depositing tellurium on the substrate from vapor of a tellurium precursor selected from among:
(i) Te(IV) organyls having the formula $TeR^1R^2R^3R^4$ wherein each of $R^1$, $R^2$, $R^3$ and $R^4$ is the same as or different from others, and each is independently selected from H, halogen, $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl and acetylalkyl;
(ii) tellurium bis-amides of the formula $Te[NR_2]_2$ wherein each R is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl;
(iii) asymmetric tellurium compounds including one alkyl substituent and a second ligand containing a heteroatom;
(iv) tellurium compounds with ethylenediamine ligands;
(v) tellurium compounds with dithiocarbamate ligands;
(vi) Te(II) and Te(IV) compounds including at least one nitrogen-based ligand selected from among amidinates, guanidinates, isoureates and beta-diketoiminates; and
(vii) dialkyl ditellurides wherein alkyl is $C_1$-$C_8$ alkyl.

The invention in another aspect relates to a method of making a PCRAM device, comprising forming a GST film on a substrate for fabrication of said device, wherein said forming comprises depositing tellurium on the substrate from vapor of a tellurium precursor selected from among:
(i) Te(IV) organyls having the formula $TeR^1R^2R^3R^4$ wherein each of $R^1$, $R^2$, $R^3$ and $R^4$ is the same as or different from others, and each is independently selected from H, halogen, $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl and acetylalkyl;
(ii) tellurium bis-amides of the formula $Te[NR_2]_2$ wherein each R is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl;
(iii) asymmetric tellurium compounds including one alkyl substituent and a second ligand containing a heteroatom;
(iv) tellurium compounds with ethylenediamine ligands;
(v) tellurium compounds with dithiocarbamate ligands;
(vi) Te(II) and Te(IV) compounds including at least one nitrogen-based ligand selected from among amidinates, guanidinates, isoureates and beta-diketoiminates; and
(vii) dialkyl ditellurides wherein alkyl is $C_1$-$C_8$ alkyl.

The invention in a further aspect relates to a tellurium compound including at least one ethylenediamide ligand, wherein tellurium is in oxidation state (II) or (IV).

Another aspect of the invention relates to a tellurium (IV) compound selected from the group consisting of:

N,N'-di-tert-butylethylenediamide telluriumdichloride;

2,5-Bis(tert-butyl)-2,5-diaza-1-telluracyclopentane dichloride;

N-methyl,N'-tert-butylethylenediamide telluriumdichloride;

N,N'-di-tert-butyl-2,3-dimethylethylenediamide telluriumdichloride; and

N,N'-di-tert-butylethylenediamide telluriumchloride dimethylamide.

An additional aspect of the invention relates to a tellurium (IV) compound of the formula:

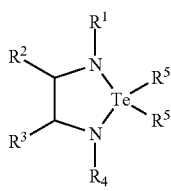

wherein:
$R^1$, $R^2$, $R^3$, $R^4$ and $R^5$ are the same as or different from one another, and each is independently selected from $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkylamine, alkoxyalkyl, aryloxyalkyl, imidoalkyl, acetylalkyl and halogen (chlorine, bromine, iodine or fluorine), and each $R^5$ can additionally and independently be hydrogen or amide.

In a further aspect, the invention relates to a tellurium (II) compound of the formula:

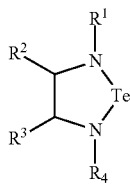

wherein:
$R^1$, $R^2$, $R^3$ and $R^4$ are the same as or different from one another, and each is independently selected from $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl, acetylalkyl and halogen (chlorine, bromine, iodine or fluorine), and $R^2$ and $R^3$ can additionally and independently be hydrogen.

A still further aspect of the invention relates to a method of forming a tellurium or tellurium-containing film on a substrate, comprising volatilizing a tellurium compound as described above, to form a tellurium precursor vapor, and contacting the tellurium precursor vapor with the substrate to deposit tellurium thereon.

In another aspect, the invention relates to a method of making a tellurium (IV) compound, comprising the following reaction:

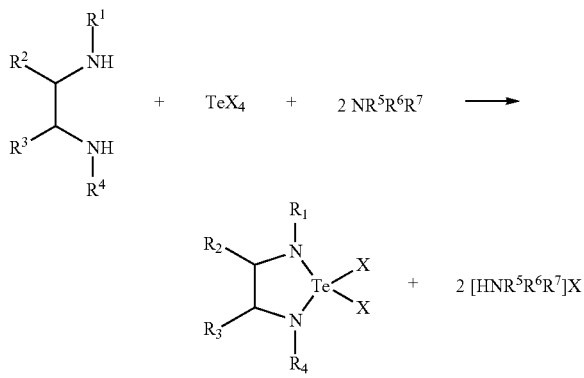

wherein:
$R^1$, $R^2$, $R^3$, $R^4$, $R^5$, $R^6$ and $R^7$ are the same as or different from one another, and each is independently selected from $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl, acetylalkyl and halogen (chlorine, bromine, iodine or fluorine), and $R^2$ and $R^3$ can additionally and independently be hydrogen; and X is halogen (chlorine, bromine, iodine or fluorine).

A further aspect of the invention relates to a method of making a tellurium (IV) compound, comprising the following reaction:

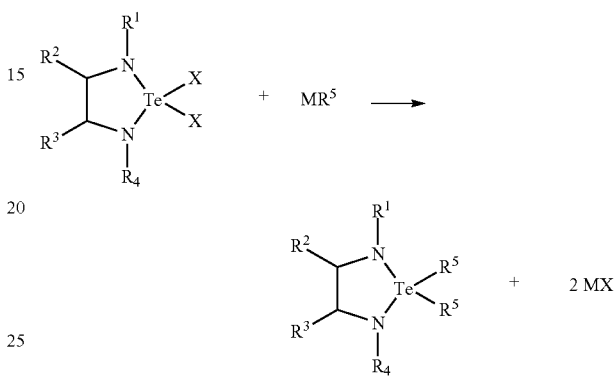

wherein:
$R^1$, $R^2$, $R^3$, $R^4$ and $R^5$ are the same as or different from one another, and each is independently selected from $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkylamine, alkoxyalkyl, aryloxyalkyl, imidoalkyl, acetylalkyl and halogen (chlorine, bromine, iodine or fluorine), and each $R^5$ can additionally and independently be hydrogen or amide;

X is a halogen (chlorine, bromine, iodine or fluorine); and

M is lithium, sodium or potassium.

In an additional aspect, the invention relates to N,N'-di-tert-butylethylenediamide telluriumdichloride.

A further aspect of the invention relates to NHTe(Cl)NMe₂.

In yet another aspect, the invention relates to a method of making a tellurium (II) compound, comprising one of the following reactions (A)-(C):

(A)

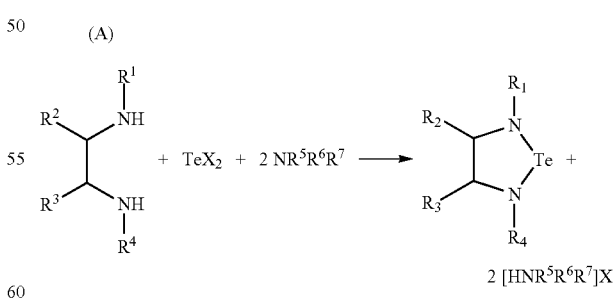

wherein:
$R^1$, $R^2$, $R^3$, $R^4$, $R^5$, $R^6$ and $R^7$ are the same as or different from one another, and each is independently selected from $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl, acetylalkyl and halogen (chlorine, bromine, iodine or fluorine), and $R^2$ and $R^3$ can additionally and independently be hydrogen; and
X is halogen (chlorine, bromine, iodine or fluorine);

(B)

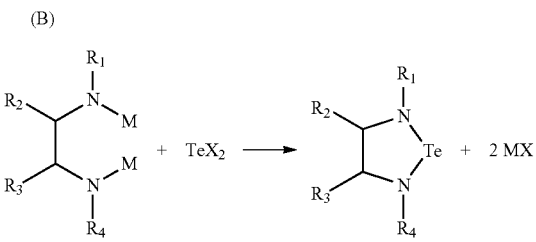

wherein:
M=Li, Na, K;
X=chlorine, bromine, iodine or fluorine;
$R_1$, $R_2$, $R_3$, $R_4$ can be the same as or different from one another, and each is independently selected from $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl, acetylalkyl and halogen (chlorine, bromine, iodine or fluorine); and (C)

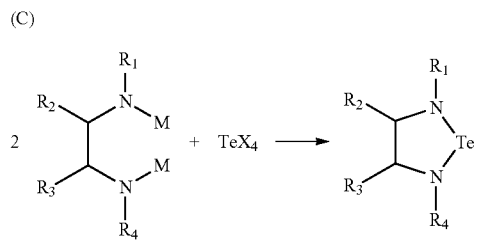

wherein:
M=Li, Na, or K;
X=Cl, Br, I or F;
$R_1$, $R_2$, $R_3$, $R_4$ can be the same as or different from one another, and each is independently selected from $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl, acetylalkyl, hydrogen and halogen (chlorine, bromine, iodine or fluorine).

A further aspect of the invention relates to a method of making a tellurium (II) compound, comprising the following reaction:

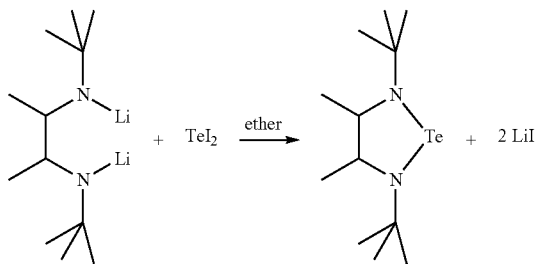

A further aspect of the invention relates to a diorgano ditelluride compound comprising organo groups each of which is selected from $C_1$-$C_{12}$ hydrocarbyl groups, silyl and substituted silyl.

The invention also pertains to a method of forming a tellurium or tellurium-containing film on a substrate, comprising vaporizing $Te_2(t-Bu)_2$ to form a corresponding vapor, and contacting said vapor with said substrate to form said tellurium or tellurium-containing film thereon.

Still another aspect of the invention relates to a packaged tellurium reagent, comprising a reagent storage and dispensing vessel containing a tellurium reagent of a type as described above.

In one aspect, the invention further relates to a method of combating pre-reaction of precursors described herein in a vapor deposition process for forming a film on a substrate, wherein the precursors described herein are susceptible to pre-reaction adversely affecting the film. In this aspect, the method involves introducing to the process a pre-reaction-combating agent selected from the group consisting of (i) heteroatom (O, N, S) organo Lewis base compounds, (ii) free radical inhibitors, and (iii) deuterium-containing reagents.

Another aspect of the invention relates to a method of combating pre-reaction of the precursors described in a vapor deposition process in which multiple feed streams are flowed to a deposition locus to form a film on a substrate, wherein at least one of said multiple feed streams includes a precursor susceptible to pre-reaction adversely affecting the film. The method involves introducing to at least one of said multiple feed streams or supplied materials therefor, or to the deposition locus, a pre-reaction-combating agent selected from the group consisting of (i) heteroatom (O, N, S) organo Lewis base compounds, (ii) free radical inhibitors, and (iii) deuterium-containing reagents.

A still further aspect of the invention relates to a composition, comprising a precursor as described herein and a pre-reaction-combating agent for said precursor, said pre-reaction-combating agent being selected from the group consisting of (i) heteroatom (O, N, S) organo Lewis base compounds, (ii) free radical inhibitors, and (iii) deuterium-containing reagents.

In a further aspect, the invention relates to a method of combating pre-reaction of a vapor phase precursor described herein in contact with a substrate for deposition of a film component thereon. The method involves contacting said substrate, prior to said contact of the vapor phase precursor therewith, with a pre-reaction-combating agent selected from the group consisting of (i) heteroatom (O, N, S) organo Lewis base compounds, (ii) free radical inhibitors, and (iii) deuterium-containing reagents.

In a further aspect, the invention relates to a process wherein the pre-reaction combating reagent is introduced to passivate the surface of a growing film or slow the deposition rate, followed by reactivation using an alternative precursor or co-reactant (for example $H_2$, $NH_3$, plasma, $H_2O$, hydrogen sulfide, hydrogen selenide, diorganotellurides, diorganosulfides, diorganoselenides, etc.). Such passivation/retardation followed by reactivation thus may be carried out in an alternating repetitive sequence, for as many repetitive cycles as desired, in ALD or ALD-like processes. Pre-reaction-combating agents can be selected from the group consisting of (i) heteroatom (O, N, S) organo Lewis base compounds, (ii) free radical inhibitors, and (iii) deuterium-containing reagents.

Another aspect of the invention relates to a vapor phase deposition process for forming a film on a substrate involving cyclic contacting of the substrate with at least one film precursor described herein that is undesirably pre-reactive in the vapor phase. The process involves introducing to said film during growth thereof a pre-reaction-combating reagent that is effective to passivate a surface of said film or to slow rate of deposition of said film precursor, and after introducing said pre-reaction-combating reagent, reactivating said film with a different film precursor.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
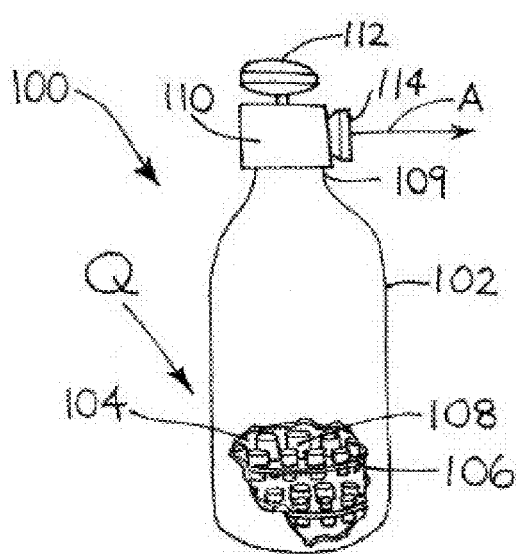
FIG. 1 is a schematic representation of a material storage and dispensing package containing a precursor of the present invention, in one embodiment thereof.

The present invention relates to tellurium precursors useful in film-forming applications, e.g., in chemical vapor deposition and atomic layer deposition applications, to form corresponding tellurium-containing films on substrates, as well as associated processes of making and using such precursors, and packaged forms of such precursors.

As used herein, the term "film" refers to a layer of deposited material having a thickness below 1000 micrometers, e.g., from such value down to atomic monolayer thickness values. In various embodiments, film thicknesses of deposited material layers in the practice of the invention may for example be below 100, 10, or 1 micrometers, or in various thin film regimes below 200, 100, or 50 nanometers, depending on the specific application involved. As used herein, the term "thin film" means a layer of a material having a thickness below 1 micrometer.

As used herein, the singular forms "a", "and", and "the" include plural referents unless the context clearly dictates otherwise.

As used herein, the identification of a carbon number range, e.g., in $C_1$-$C_{12}$ alkyl, is intended to include each of the component carbon number moieties within such range, so that each intervening carbon number and any other stated or intervening carbon number value in that stated range, is encompassed, it being further understood that sub-ranges of carbon number within specified carbon number ranges may independently be included in smaller carbon number ranges, within the scope of the invention, and that ranges of carbon numbers specifically excluding a carbon number or numbers are included in the invention, and sub-ranges excluding either or both of carbon number limits of specified ranges are also included in the invention. Accordingly, $C_1$-$C_{12}$ alkyl is intended to include methyl, ethyl, propyl, butyl, pentyl, hexyl, heptyl, octyl, nonyl, decyl, undecyl and dodecyl, including straight chain as well as branched groups of such types. It therefore is to be appreciated that identification of a carbon number range, e.g., $C_1$-$C_{12}$, as broadly applicable to a substituent moiety, enables, in specific embodiments of the invention, the carbon number range to be further restricted, as a sub-group of moieties having a carbon number range within the broader specification of the substituent moiety. By way of example, the carbon number range $C_1$-$C_{12}$ alkyl, may be more restrictively specified, in particular embodiments of the invention, to encompass sub-ranges such as $C_1$-$C_4$ alkyl, $C_2$-$C_8$ alkyl, $C_2$-$C_4$ alkyl, $C_3$-$C_5$ alkyl, or any other sub-range within the broad carbon number range.

The precursors of the invention may be further specified in specific embodiments by provisos or limitations excluding specific substituents, groups, moieties or structures, in relation to various specifications and exemplifications thereof set forth herein. Thus, the invention contemplates restrictively defined compositions, e.g., a composition wherein $R^1$ is $C_1$-$C_{12}$ alkyl, with the proviso that $R^i \neq C_4$ alkyl when $R^j$ is silyl.

The invention relates in one aspect to Te(IV) organyls useful for low temperature (T<400° C.) deposition of Te-containing films, e.g., for forming germanium-antimony-tellurium (GST) films such as Ge$_2$Sb$_2$Te$_5$ on substrates such as wafers in the production of phase change random access memory devices.

The Te(IV) organyls of the invention are suitable for forming such films by techniques such as atomic layer deposition (ALD) and chemical vapor deposition (CVD). Preferred precursors of such type are liquid at room temperature (25° C.) and have high volatility and desirable transport properties for ALD and CVD applications.

In accordance with another aspect of the invention, Te(IV) organyls having the formula TeR$^1$R$^2$R$^3$R$^4$ wherein R$^1$, R$^2$, R$^3$ and R$^4$ are organo substituents, are employed to form Te-containing highly conformal films of superior character by a vapor deposition process such as ALD or CVD.

In a preferred aspect, Te(IV) organyls are utilized having the formula TeR$^1$R$^2$R$^3$R$^4$ wherein each of R$^1$, R$^2$, R$^3$ and R$^4$ is the same as or different from others, and each is independently selected from H, halogen (fluorine, bromine, iodine and chlorine), $C_1$-$C_6$ alkyl, $C_1$-$C_6$ alkoxy, $C_3$-$C_8$ cycloalkyl, $C_6$-$C_{10}$ aryl, silyl, substituted silyl (silyl having $C_1$-$C_6$ alkyl substituents and/or $C_6$-$C_{10}$ aryl substituents), amide, aminoalkyl, alkylamine, alkoxyalkyl, aryloxyalkyl, imidoalkyl and acetylalkyl. The alkyl moiety in such aminoalkyl, alkylamine, alkoxyalkyl, aryloxyalkyl, imidoalkyl and acetylalkyl substituents can be $C_1$-$C_6$ alkyl or alkyl moieties of other carbon numbers, as may be useful in a given application of such organyl compounds.

Tellurium(IV) organyls of the invention useful for the aforementioned film-forming applications can readily be formed by the following generalized reaction:

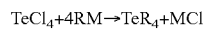

TeCl$_4$+4RM→TeR$_4$+MCl wherein M is Li or MgX, X is halide, and each R independently may be H, halogen (fluorine, bromine, iodine and chlorine), $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl or acetylalkyl, as above described.

The Te(IV) compounds of the invention are usefully employed as CVD/ALD precursors for the deposition of Te-containing films, e.g., by liquid delivery techniques in which such compounds are provided in compositions including suitable solvent media. Useful solvents for such purpose in specific applications may include, without limitation, alkanes (e.g., hexane, heptane, octane, and pentane), aromatics (e.g., benzene or toluene), and amines (e.g., triethylamine, tert-butylamine). The solvent medium in which the Te precursor or precursors are dissolved or suspended may be a single-component solvent or a multi-component solvent composition.

The precursors when in a liquid state can also be delivered neat using ALD/CVD liquid delivery techniques, in which the liquid is volatilized to form a corresponding precursor vapor, which then is contacted with the substrate on which the tellurium-containing film is to be formed, under appropriate vapor deposition conditions.

When the precursors are in a solid state, they may be volatilized for delivery using any suitable solid delivery system, such as the solid delivery and vaporizer unit commercially available under the trademark ProE-Vap from ATMI, Inc. (Danbury, Conn., USA). The precursor or precursors (since the invention contemplates use of multiple Te precursors of differing type) are volatilized to form the corresponding precursor vapor which then is contacted with a wafer or other substrate to deposit a tellurium-containing layer thereon.

The precursor vapor formed from the Te precursor may be mixed with carrier or co-reactant gases in various embodiments, to obtain desired deposition thicknesses, growth rates, etc., as will be apparent to those skilled in the art.

The present invention in various aspects involves compositions and methods in which tellurium dialkyls and ditellurium dialkyls can be utilized as tellurium source reagents, but in other aspects, non-alkyl tellurium and non-alkyl ditellurium compounds are utilized.

The invention in a further aspect relates to a synthetic route for the preparation of tellurium amide compounds, e.g., tellurium bis-amides that are useful for low temperature deposition of tellurium amides on substrates.

The tellurium amide compounds can be formed by reacting tellurium dihalide with two equivalents of a metal amide, according to the following reaction.

$$TeX_2 + 2MNR_2 \rightarrow Te[NR_2]_2 + 2MX$$

wherein:
X is halogen, preferably Cl, Br or I,
M is Li, Na, or K, and
each R is independently selected from among H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl, as above described.

In one preferred embodiment, $TeI_e$ is reacted with $LiN(t\text{-}Bu)(SiMe_3)$ to form the reaction product $Te[N(t\text{-}Bu)(SiMe_3)]_2$.

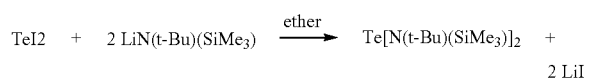

wherein t-butyl is tertiary butyl, and Me is methyl.

This product, $Te[N(t\text{-}Bu)(SiMe_3)]_2$, has been characterized by NMR spectroscopy and thermal analysis (STA), as a low melting solid (mp=77° C.) that shows good transport properties (T50=184° C.) and low residual mass (<2%). This compound is usefully employed as a precursor for the low temperature deposition of tellurium-containing films.

In another preferred embodiment, $TeI_2$ is reacted with $KN(SiMe_3)_2$ to form the following reaction product, $Te[N(SiMe_3)_2]_2$.

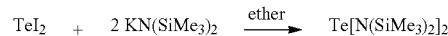

A further aspect of the invention relates to asymmetric tellurium compounds including one alkyl substituent and a second ligand containing a heteroatom, e.g., nitrogen or sulfur. The second ligand may be of any suitable type, and in specific embodiments is amidinate, guanidinate, or dithiocarbamate.

In one embodiment, the starting material for the asymmetric tellurium compound is $ITeNR^1R^2$ wherein each of $R^1$ and $R^2$ is the same as or different from the other, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl, as above described. This starting material can be synthesized by the reaction of $TeI_2$ with one equivalent of a lithium amide as shown below.

or, more generally, halide starting materials can be formed according to the following reaction.

$$TeX_2 + MNR_1R_2 \rightarrow XTeNR_1R_2 + MX$$

wherein
M is Li, Na, or K, preferably Li,
X is halogen, preferably Cl, Br or I, and each of $R_1$ and $R_2$ is the same as or different from the other, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl, as above described.

The starting material $ITeNR^1R^2$ is extremely sensitive to light and air when isolated as an orange solid product, however, it can be placed into solution with a suitable solvent medium, e.g., a hydrocarbon solvent medium, containing pentane, hexane or toluene, or other hydrocarbon species. Such starting material $ITeNR^1R^2$ can be reacted in situ in the hydrocarbon solvent medium with an alkyl lithium reagent to obtain an asymmetric tellurium compound, as shown in the reaction below.

$$XTeNR^1R^2 + MR^3 \rightarrow R^3TeNR^1R^2 + MX$$

wherein
M is Li, Na, or K, preferably Li,
X is halogen, preferably Cl, Br or I, and each of $R^1$, $R^2$ and $R^3$ is the same as or different from the other, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl, as above described, and wherein $R^3$ can in addition be amide or halogen.

Using the same synthetic approach, other ligands, such as:

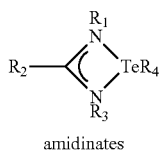

amidinates wherein each of $R_1$, $R_2$, $R_3$ and $R_4$ is the same as or different from others, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl, and wherein $R_4$ can in addition be halogen or amide;

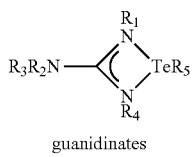

guanidinates wherein each of $R_1$, $R_2$, $R_3$, $R_4$ and $R_5$ is the same as or different from others, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl, and wherein $R_5$ can in addition be halogen or amide; and

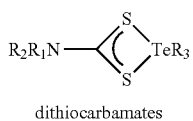

dithiocarbamates wherein each of $R_1$, $R_2$ and $R_3$ is the same as or different from others, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, alkoxyalkyl, aryloxyalkyl, imidoalkyl and acetylalkyl and wherein $R^3$ can in addition be halogen or amide, can be synthesized as well.

The invention therefore provides asymmetric tellurium compounds including tellurium amides, amidinates, guanidinates and dithiocarbamates of a useful character for ALD or CVD deposition of tellurium or tellurium-containing films, e.g., for fabricating GST devices comprising $Ge_2Sb_2Te_5$ films.

Another aspect of the invention relates to tellurium compounds with ethylenediamine ligands and tellurium compounds with dithiocarbamate ligands, for use in low temperature deposition applications such as fabrication of the aforementioned GST-based phase change memory devices.

Tellurium complexes with ethylenediamine type ligands can be synthesized, according to one preferred aspect of the invention, by reacting a lithium salt of the ethylenediamine with a tellurium halide, such as $TeX_2$ or $TeX_4$, wherein X is halogen. From the resulting reaction product, the desired tellurium compounds can be obtained by a salt elimination reaction.

The following reaction scheme therefore may be used for production of such tellurium precursors.

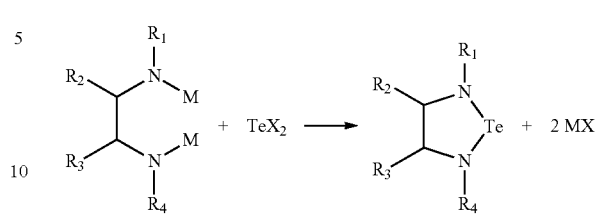

wherein
M=Li, Na, or K;
X=Cl, Br, or I;
each of $R^1$, $R^2$, $R^3$ and $R^4$ is the same as or different from others, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl.

Alternatively, the following reaction scheme can be employed to produce the tellurium ethylenediamine precursors.

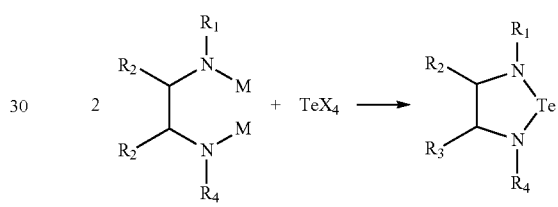

wherein
M=Li, Na, or K;
X=Cl, Br, or I;
each of $R^1$, $R^2$, $R^3$ and $R^4$ is the same as or different from others, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl.

A specific synthesis procedure for forming a tellurium precursor with ethylenediamine ligands is set forth below.

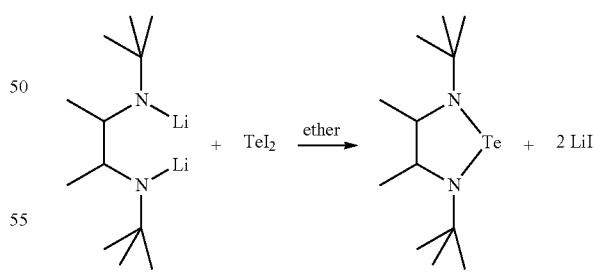

Tellurium ethylenediamine compounds of such type have high volatility and low decomposition temperatures, and thus are well suited for ALD and CVD applications.

Complexes of tellurium with only dithiocarbamate ligands, or including dithiocarbamate and other co-ligands, constitute a further group of precursors useful for ALD and CVD in accordance with the invention. Tellurium dithiocarbamate precursors of the invention include the following classes (a)-(e):

(a)

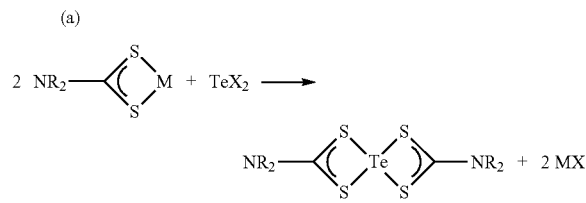

wherein

M is Li, Na, or K, preferably Li,

X is halogen, preferably Cl, Br or I, and each R is the same as or different from the other, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl;

(b)

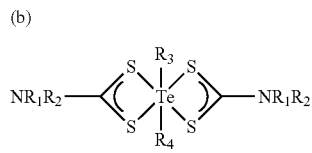

wherein each of $R_1$, $R_2$, $R_3$ and $R_4$ is the same as or different from others, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl, and wherein $R_3$ and $R_4$ can in addition and independently be halogen or amide;

(c)

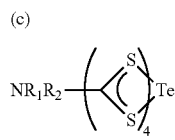

wherein each of $R_1$ and $R_2$ is the same as or different from the other, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl;

(d)

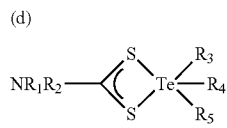

wherein:

each of $R_1$, $R_2$, $R_3$, $R_4$ and $R_5$ is the same as or different from others, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl, and wherein each of $R_3$, $R_4$ and $R_5$ can in addition and independently be amide or halogen; and (e)

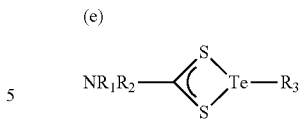

wherein each of $R_1$, $R_2$ and $R_3$ is the same as or different from others, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl, and wherein $R_3$ can in addition be halogen or amide.

These precursors accommodate low temperature deposition applications, having good volatilization and transport properties. They can be delivered in a neat form in the case of precursor compounds in liquid form, or in compositions including suitable solvent media. Useful solvents for such purpose in specific applications may include, without limitation, alkanes (e.g., hexane, heptane, octane, and pentane), aromatics (e.g., benzene or toluene), and amines (e.g., triethylamine, tert-butylamine) or mixtures thereof, as above described.

The precursors when in a solid state can be volatilized for delivery using any suitable solid delivery system, such as the solid delivery and vaporizer unit commercially available under the trademark ProE-Vap from ATMI, Inc. (Danbury, Conn., USA). The precursor or precursors (since the invention contemplates use of multiple Te precursors of differing type) are volatilized to form the corresponding precursor vapor which then is contacted with a wafer or other substrate to deposit a tellurium-containing layer thereon, e.g., for forming a GST layer.

The invention in yet another aspect relates to tellurium compounds with nitrogen donor ligands useful for deposition applications to deposit tellurium or tellurium-containing films on substrates, for applications such as GST phase change random access memory (PRAM) devices.

This aspect of the invention relates more specifically to Te(II) and Te(IV) precursors having at least one nitrogen-based ligand selected from among amidinates, guanidinates, isoureates and beta-diketoiminates.

Specific tellurium nitrogen donor ligand precursors of the invention include the following:

(A) Te(II) amidinates, guanidinates, and isoureates of the formula

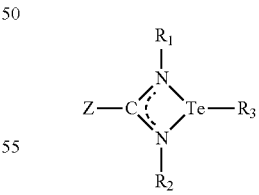

wherein:

each of $R_1$, $R_2$ and $R_3$ is the same as or different from others, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl, and wherein $R^3$ can in addition be halogen or amide; and Z is independently selected from $C_1$-$C_6$ alkoxy, —$NR_1R_2$, H, $C_1$-$C_6$ alkyl, $C_3$-$C_{10}$ cycloalkyl, and $C_6$-$C_{13}$ aryl;

(B) Te(IV) amidinates, guanidinates, and isoureates of the formula

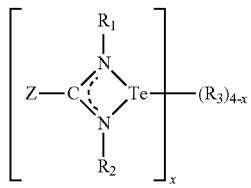

wherein:
each of $R_1$, $R_2$ and $R_3$ is the same as or different from others, and each is independently selected from H, $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkoxyalkyl, aryloxyalkyl, imidoalkyl and acetylalkyl, and wherein each $R_3$ can in addition and independently be halogen or amide;
Z is independently selected from $C_1$-$C_6$ alkoxy, —$NR_1R_2$, H, $C_1$-$C_6$ alkyl, $C_3$-$C_{10}$ cycloalkyl, and $C_6$-$C_{13}$ aryl; and
x is an integer having a value of from 0 to 4, inclusive;
(C) Te(II) beta-diketoiminates of the formula

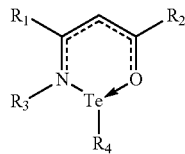

wherein
each of $R_1$, $R_2$, $R_3$ and $R_4$ is the same as or different from others, and each is independently selected from H, halogen, $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl and acetylalkyl; and
(D) Te(IV) beta-diketoiminates of the formula

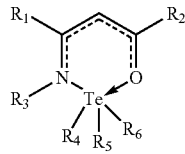

wherein
each of $R_1$, $R_2$, $R_3$, $R_4$, $R_5$ and $R_6$ is the same as or different from others, and each is independently selected from H, halogen, $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl and acetylalkyl.

The tellurium compounds of the invention in film formation processes may be used with appropriate co-reactants, e.g., in a continuous deposition mode (CVD) or pulsed/atomic layer deposition mode (ALD), to deposit films of superior character. For oxides, preferred co-reactants include $O_2$ and $N_2O$ for CVD, and more aggressive oxidizers for pulsed deposition, e.g., $H_2O$, ozone, and $O_2$ plasma. For metal-like films, reducing atmospheres are advantageously used.

The precursors of the invention can be utilized as low temperature deposition precursors with reducing co-reactants such as hydrogen, $H_2$/plasma, amines, imines, hydrazines, silanes, germanes such as $GeH_4$, ammonia, alkanes, alkenes and alkynes. For CVD modes of film formation, reducing agents such as $H_2$, and $NH_3$ are preferred, and plasmas of these co-reactants may be used in digital or ALD mode, wherein the co-reactants are separated from the precursor in a pulse train, utilizing general CVD and ALD techniques within the skill of the art, based on the disclosure herein. More aggressive reducing agents can also be used in a digital or ALD mode since co-reactants can be separated, preventing gas phase reactions. For ALD and conformal coverage in high aspect ratio structures, the precursor preferably exhibits self-limiting behavior in one type of atmosphere (e.g., inert or weakly reducing/oxidizing gas environments) and exhibits rapid decomposition to form a desired film in another type of atmosphere (e.g., plasma, strongly reducing/oxidizing environments).

Liquid delivery formulations can be employed in which precursors that are liquids may be used in neat liquid form, or liquid or solid precursors may be employed in suitable solvents, including for example alkane solvents (e.g., hexane, heptane, octane, and pentane), aryl solvents (e.g., benzene or toluene), amines (e.g., triethylamine, tert-butylamine), imines and hydrazines or mixtures thereof. The utility of specific solvent compositions for particular Te precursors may be readily empirically determined, to select an appropriate single component or multiple component solvent medium for the liquid delivery vaporization and transport of the specific tellurium precursor that is employed. In the case of solid precursors of the invention, a solid delivery system may be utilized, for example, using the ProE-Vap solid delivery and vaporizer unit (commercially available from ATMI, Inc., Danbury, Conn., USA).

In general, the thicknesses of metal-containing layers formed using the precursors of the invention can be of any suitable value. In a specific embodiment of the invention, the thickness of the tellurium-containing layer can be in a range of from 5 nm to 500 nm or more.

The various tellurium precursor compounds of the invention can be utilized to form GST films in combination any with suitable germanium and antimony precursors, e.g., by CVD and ALD techniques, for applications such as PCRAM device manufacture. The process conditions useful for carrying out deposition of Te-containing films can be readily determined within the skill of the art by the simple expedient of selectively varying the delivery and deposition process conditions and characterizing the resulting films, to determine the process conditions envelope most appropriate for a given deposition application.

In one specific embodiment of the invention, Te[N(SiMe$_3$)$_2$]$_2$ is used as a tellurium precursor for forming tellurium-containing films on substrates, such as GST films, amorphous GeTe films, and SbTe films, by atomic layer deposition (ALD) and chemical vapor deposition (CVD) techniques.

In another embodiment, amorphous GeTe and SbTe are deposited from di-t-butyl tellurium, Te(tBu)$_2$, at temperature in a range of from 300° C.-350° C., e.g., 320° C., using bubbler delivery of the tellurium precursor in an inert carrier gas stream, e.g., $N_2$ at a flow rate of 20-50 sccm, e.g., 30 sccm. The respective germanium and antimony precursors used for such deposition can be of any suitable types, e.g., GeBAMDN, SbTDMA, etc., and such precursors can be delivered for deposition at any suitable volumetric flow rate, e.g., for the aforementioned flow rate of 30 sccm for the illustrative tellurium precursor, Te(tBu)$_2$, a flow rate of such Ge or Sb precursor can be on the order of 5 micromoles/ minute. The resulting amorphous GeTe and SbTe films will have a tellurium content of approximately 40%.

FIG. 1 is a schematic representation of a material storage and dispensing package 100 containing a tellurium precursor, according to one embodiment of the present invention.

The material storage and dispensing package 100 includes a vessel 102 that may for example be of generally cylindrical shape as illustrated, defining an interior volume 104 therein. In this specific embodiment, the precursor is a solid at ambient temperature conditions, and such precursor may be supported on surfaces of the trays 106 disposed in the interior volume 104 of the vessel, with the trays having flow passage conduits 108 associated therewith, for flow of vapor upwardly in the vessel to the valve head assembly for dispensing, in use of the vessel.

The solid precursor can be coated on interior surfaces in the interior volume of the vessel, e.g., on the surfaces of the trays 106 and conduits 108. Such coating may be effected by introduction of the precursor into the vessel in a vapor form from which the solid precursor is condensed in a film on the surfaces in the vessel. Alternatively, the precursor solid may be dissolved or suspended in a solvent medium and deposited on surfaces in the interior volume of the vessel by solvent evaporation. In yet another method the precursor may be melted and poured onto the surfaces in the interior volume of the vessel. For such purpose, the vessel may contain substrate articles or elements that provide additional surface area in the vessel for support of the precursor film thereon.

As a still further alternative, the solid precursor may be provided in granular or finely divided form, which is poured into the vessel to be retained on the top supporting surfaces of the respective trays 106 therein. As a further alternative, a metal foam body may be provided in the interior volume of the vessel, which contains porosity of a specific character adapted for retaining the solid particulate precursor for highly efficient vaporization thereof.

The vessel 102 has a neck portion 109 to which is joined the valve head assembly 110. The valve head assembly is equipped with a hand wheel 112 in the embodiment shown. In lieu of a hand wheel, the valve head assembly may in turn be coupled or operatively linked to a controller for automated operation. The valve head assembly 110 includes a dispensing port 114, which may be configured for coupling to a fitting or connection element to join flow circuitry to the vessel. Such flow circuitry is schematically represented by arrow A in FIG. 1, and the flow circuitry may be coupled to a downstream ALD or chemical vapor deposition chamber (not shown in FIG. 1).

In use, the vessel 102 can be heated with a suitable heater, such as a heating jacket, resistance heating elements affixed to the exterior wall surface of the vessel, etc., so that solid precursor in the vessel is at least partially volatilized to provide precursor vapor. The input of heat is schematically shown in FIG. 1 by the reference arrow Q. The precursor vapor is discharged from the vessel through the valve passages in the valve head assembly 110 when the hand wheel 112 or alternative valve actuator or controller is translated so that the valve is in an open position, whereupon vapor deriving from the precursor is dispensed into the flow circuitry schematically indicated by arrow A.

In lieu of solid delivery of the precursor, the precursor may be provided in a solvent medium, forming a solution or suspension. Such precursor-containing solvent composition then may be delivered by liquid delivery and flash vaporized to produce a precursor vapor. The precursor vapor is contacted with a substrate under deposition conditions, to deposit the metal on the substrate as a film thereon.

In one embodiment, the precursor is dissolved in an ionic liquid medium, from which precursor vapor is withdrawn from the ionic liquid solution under dispensing conditions.

As a still further alternative, the precursor may be stored in an adsorbed state on a suitable solid-phase physical adsorbent storage medium in the interior volume of the vessel. In use, the precursor vapor is dispensed from the vessel under dispensing conditions involving desorption of the adsorbed precursor from the solid-phase physical adsorbent storage medium.

Supply vessels for precursor delivery may be of widely varying type, and may employ vessels such as those commercially available from ATMI, Inc. (Danbury, Conn.) under the trademarks SDS, SAGE, VAC, VACSorb, and ProE-Vap, as may be appropriate in a given storage and dispensing application for a particular precursor of the invention.

The precursors of the invention thus may be employed to form precursor vapor for contacting with a substrate to deposit a tellurium-containing thin film thereon.

In a preferred aspect, the invention utilizes the precursors to conduct atomic layer deposition, yielding ALD films of superior conformality that are uniformly coated on the substrate with high step coverage and conformality even on high aspect ratio structures.

Accordingly, the precursors of the present invention enable a wide variety of microelectronic devices, e.g., semiconductor products, flat panel displays, etc., to be fabricated with tellurium-containing films of superior quality.

The invention in another aspect relates to a class of tellurium compounds with ethylenediamide-type ligands. Such tellurium compounds are useful as precursors for low temperature ALD/CVD of tellurium or tellurium-containing thin films, e.g., for applications such as fabrication of phase change memory devices based on $Ge_2Sb_2Te_5$ (GST). This class of compounds includes tellurium (Te) in the oxidation state IV, which is characterized by greater stability than commonly used tellurium precursors in the oxidation state II, thereby affording a beneficial alternative to the commonly used Te(II) precursors which are notoriously unstable with respect to air- and light-sensitivity.

These tellurium compounds are to our knowledge the first examples of tellurium amides in which tellurium is in oxidation state (IV). Examples of such tellurium (IV) amides include, without limitation:

Formula Compound $NHTeCl_2$ N,N'-di-tert-butylethylenediamide telluriumdichloride $NHTeCl_2$ 2,5-Bis(tert-butyl)-2,5-diaza-1-telluracyclopentane dichloride $MeNHTeCl_2$ N-methyl,N'-tert-butylethylenediamide telluriumdichloride $DMNHTeCl_2$ N,N'-di-tert-butyl-2,3-dimethylethylenediamide telluriumdichloride $NHTe(Cl)NMe_2$ N,N'-di-tert-butylethylenediamide telluriumchloride dimethylamide wherein the term NH is an abbreviation for "N-heterocyclic," and denotes an N-heterocyclic ring system containing tellurium.

The general synthetic concept for such tellurium (IV) compounds, described more fully below, is also potentially applicable to the synthesis of tellurium (II) compounds. The general synthetic scheme (Scheme I below) is based on reaction of a tellurium (IV) halide with an ethylenediamide type ligand, with the addition of a tertiary amine in order to scavenge the eliminated hydrochloride.

Scheme I

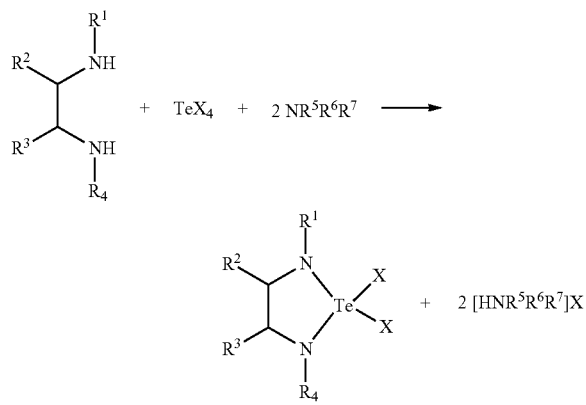

wherein:
$R^1$, $R^2$, $R^3$, $R^4$, $R^5$, $R^6$ and $R^7$ are the same as or different from one another, and each is independently selected from $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl, acetylalkyl and halogen (chlorine, bromine, iodine or fluorine), and $R^2$ and $R^3$ can additionally and independently be hydrogen; and
X is halogen (chlorine, bromine, iodine or fluorine).

Derivatives of the ethylenediamide tellurium complexes can be synthesized according to the following reaction scheme (Scheme II), by reacting the corresponding dichloride with a lithium alkyl or lithium amide species.

Scheme II

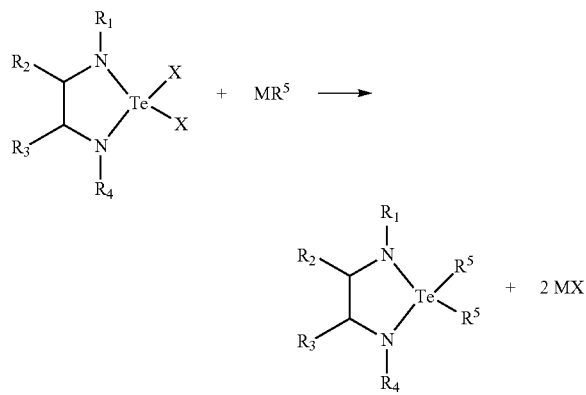

wherein:
$R^1$, $R^2$, $R^3$, $R^4$ and $R^5$ are the same as or different from one another, and each is independently selected from $C_1$-$C_6$ alkyl, $C_1$-$C_6$ alkoxy, $C_3$-$C_8$ cycloalkyl, $C_6$-$C_{10}$ aryl, silyl, substituted silyl, aminoalkyl, alkylamine, alkoxyalkyl, aryloxyalkyl, imidoalkyl, acetylalkyl and halogen (chlorine, bromine, iodine or fluorine), and each $R^5$ can additionally and independently be hydrogen or amide;
X is a halogen selected from chloride, bromide and iodide; and
M is lithium, sodium or potassium.

The foregoing synthesis reactions can be carried out in any suitable solvent medium. One preferred solvent medium comprises an ether type solvent or other somewhat polar solvent in which the tellurium halide is sufficiently soluble. Tetrahydrofuran (THF) is one preferred solvent species, while diethyl ether, dimethoxyethane and toluene are also highly advantageous species. The choice of a specific solvent medium may be readily empirically determined, based on considerations of solubility, yields and reaction times for specific desired tellurium precursor products.

Figure 2:
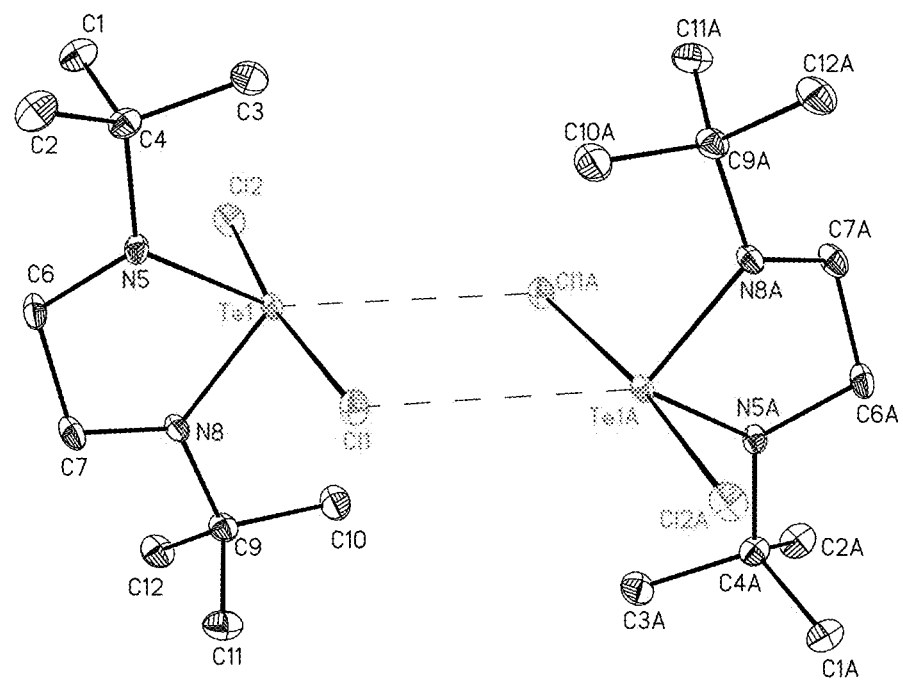
FIG. 2 is an ORTEP diagram of the structure of NHTeCl$_2$, i.e., N,N'-di-tert-butylethylenediamide telluriumdichloride.
Figure 3:
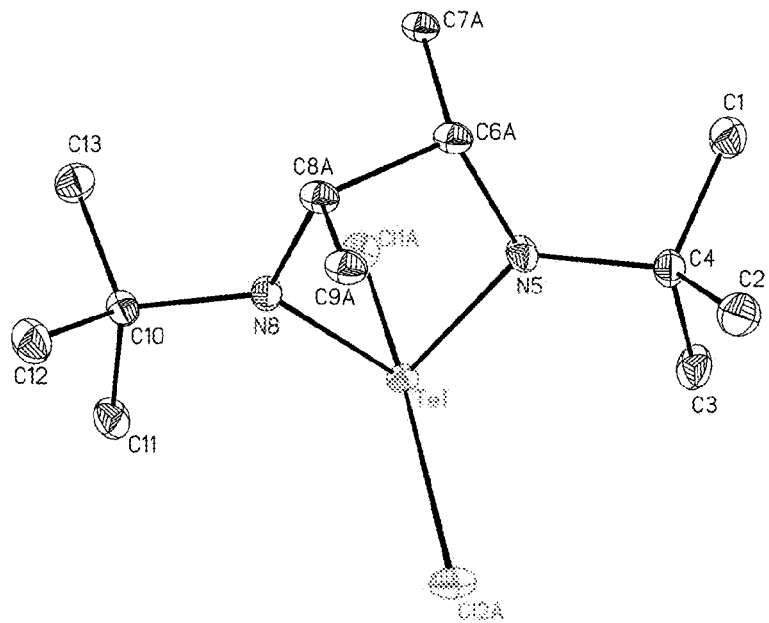
FIG. 3 is an ORTEP diagram of the structure of Me$_2$NHTeCl$_2$.

As one example of the tellurium (IV) amide compounds of the invention, FIG. 2 is an ORTEP diagram of the structure of NHTeCl$_2$, i.e., N,N'-di-tert-butylethylenediamide telluriumdichloride. This compound is readily purified to high purity by sublimation, and has been confirmed by X-ray crystal structure analysis as existing in a weakly associated dimer solid state. As another example of such tellurium (IV) amide compounds, FIG. 3 is an ORTEP diagram of the structure of Me$_2$NHTeCl$_2$, also confirmed by X-ray crystal structure analysis to exist in a weakly associated dimer solid state.

Figure 4:
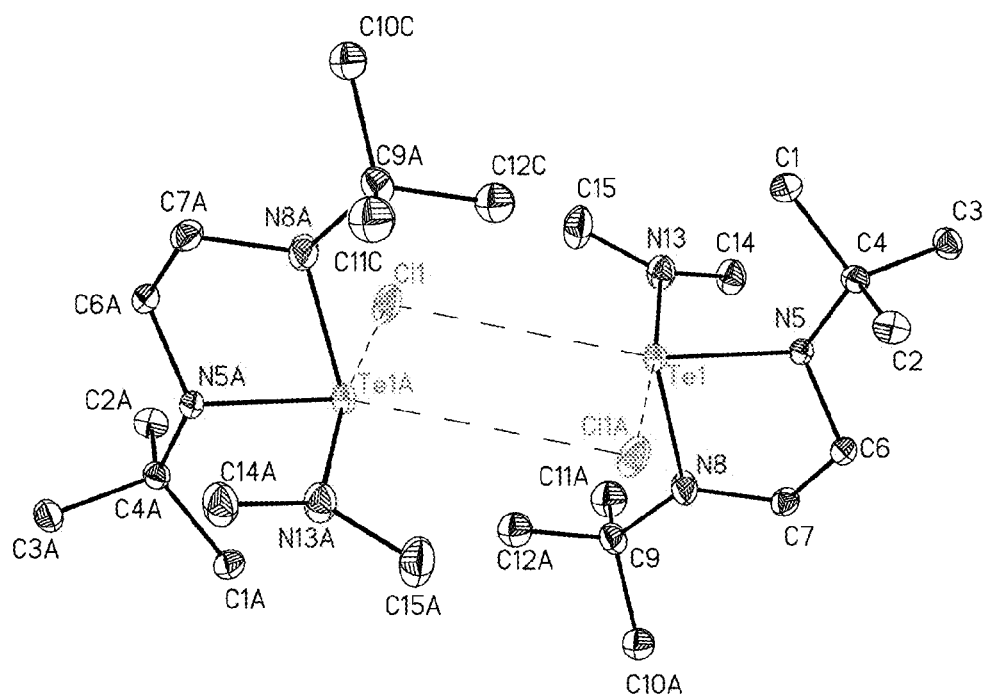
FIG. 4 is an ORTEP diagram of the structure of NHTe(Cl)NMe$_2$.

FIG. 4 is an ORTEP diagram of the structure of NHTe(Cl)NMe$_2$. This tellurium source compound can be synthesized by a reaction scheme as described above. Such reaction scheme can be utilized to produce a mono-substituted species under mild reaction conditions, e.g., stirring of the reaction volume at room temperature, while a large excess of amide and harsher conditions, such as several days under reflux conditions, can be utilized to produce the disubstituted compound.

Corresponding compounds of tellurium (II) can be synthesized by the following related reaction scheme (Scheme III) conducted in a corresponding solvent medium:

Scheme III

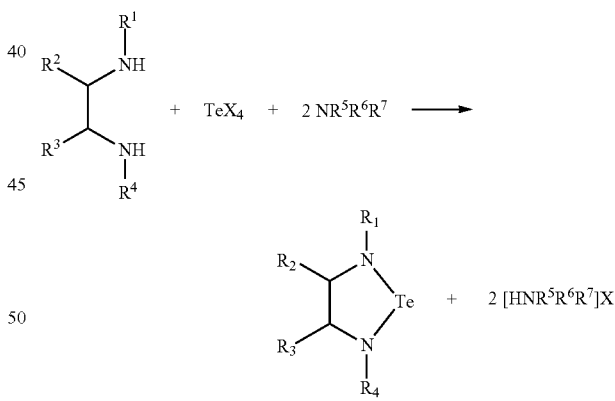

wherein:
$R^1$, $R^2$, $R^3$, $R^4$, $R^5$, $R^6$ and $R^7$ are the same as or different from one another, and each is independently selected from $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl, acetylalkyl and halogen (chlorine, bromine, iodine or fluorine), and $R^2$ and $R^3$ can additionally and independently be hydrogen; and
X is halogen (chlorine, bromine, iodine or fluorine).

Another synthesis for such tellurium (II) compounds is set out below in Scheme IIIA:

Scheme IIIA

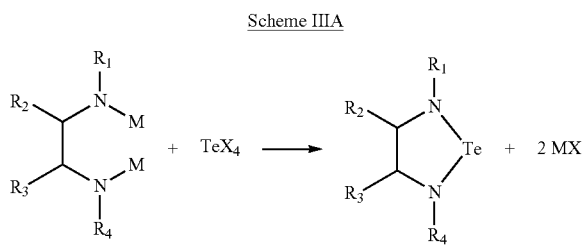

wherein:
M=Li, Na, K;
X=chlorine, bromine, iodine or fluorine;
$R_1$, $R_2$, $R_3$, $R_4$ can be the same as or different from one another, and each is independently selected from $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl, acetylalkyl and halogen (chlorine, bromine, iodine or fluorine).

A still further synthesis of such tellurium (II) compounds is set out in Scheme IIIB below:

Scheme IIIB

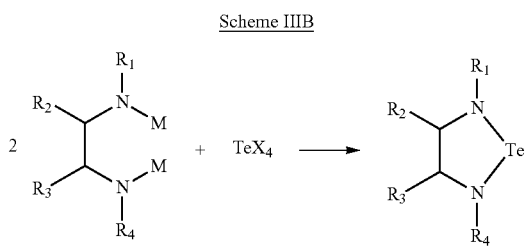

wherein:
M=Li, Na, or K;
X=Cl, Br, I or F;
$R_1$, $R_2$, $R_3$, $R_4$ can be the same as or different from one another, and each is independently selected from $C_1$-$C_6$ alkyl, $C_1$-$C_6$ alkoxy, $C_3$-$C_8$ cycloalkyl, $C_6$-$C_{10}$ aryl, silyl, substituted silyl, amide, aminoalkyl, alkylamine, alkoxyalkyl, aryloxyalkyl, imidoalkyl, acetylalkyl, hydrogen and halogen (chlorine, bromine, iodine or fluorine).

As a specific example of such tellurium (II) compounds, a synthesis of N,N'-di-tert-butyl butylenediamine tellurium is a set out below utilizing a corresponding lithiated precursor and diiodotellurium as reactants, in an ether solvent medium.

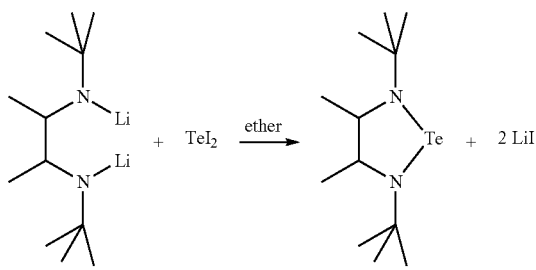

The foregoing tellurium precursors have utility in various applications for deposition of Te or Te-containing thin films. Corresponding alkyl, silyl or amide derivatives (wherein chloro substituents are replaced by alkyl or amide functional groups) can also be readily synthesized. Such alkyl or amide derivatives may be preferred in some thin film deposition applications, due to their higher volatility properties, in relation to corresponding chloro compounds having lower volatility as a result of their dimeric nature.

The invention therefore contemplates the provision of tellurium compounds in which the tellurium central metal atom is coordinated with ethylenediamine-type ligands, with the tellurium central metal atom being in a (II) or (IV) state. The invention further contemplates synthesis of ethylenediamine-type tellurium compounds substituted with alkyl and/or amide substituents. In addition, the invention contemplates use of the foregoing tellurium compounds for CVD and ALD applications, to deposit tellurium or tellurium-containing thin films.

In another aspect, the invention relates to dialkyl ditellurides useful for CVD and ALD applications carried out at low temperatures to deposit tellurium or tellurium-containing films on substrates, e.g., $Sb_2Te_3$ films for the formation of GST films in phase change memory applications.

For phase change memory applications, the tellurium precursor employed for forming GST films desirably has the ability to deposit at sufficiently low temperature to achieve amorphous $Sb_2Te_3$ films with good step coverage, since crystalline films do not provide the necessary step coverage for phase change memory device applications. The invention contemplates dialkyl ditellurides, e.g., di-tert-butyl ditelluride, to address such step coverage issues.

Dialkyl tellurides are conventionally used to deposit tellurium or tellurium-containing films by CVD or ALD in phase change memory applications, but relatively high temperatures are needed to deposit such films. This deficiency can be overcome by use of dialkyl ditellurides, e.g., di-tert-butyl ditelluride, $Te_2(t-Bu)_2$.

The reason for the lower deposition temperature achievable by this class of precursors is a relatively weak tellurium-tellurium bond. An examination of the X-ray crystal structure of $Te_2(t-Bu)_2$ reveals a fairly long Te—Te bond of 2.68 A. The lower deposition temperature is also evident from the simultaneous thermal analysis (STA) of $Te_2(t-Bu)_2$, which shows a very low T50 of 146° C. $Te_2(t-Bu)_2$ and its synthesis are described in the literature (see, for example, C. H. W. Jones, R. D. Sharma, J. of Organomet. Chem. 1983, 255, 61-70, and R. W. Gedridge Jr., K. T. Higa, R. A. Nissan, Organometallics 1991, 10, 286-291, and U.S. Pat. No. 5,166,428).

The invention therefore contemplates the use of these dialkyl ditellurides, e.g., $Te_2(t-Bu)_2$, as precursors for the deposition of tellurium or tellurium-containing films on substrates, using CVD or ALD techniques, in applications such as the manufacture of phase change memory devices.

Figure 5:
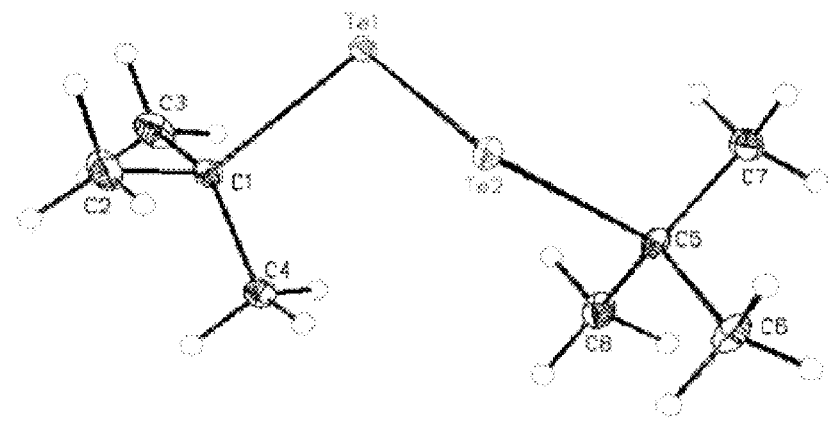
FIG. 5 is an ORTEP diagram of the structure of Te$_2$(t-Bu)$_2$.

FIG. 5 is an ORTEP diagram of the structure of $Te_2(t-Bu)_2$.

Figure 6:
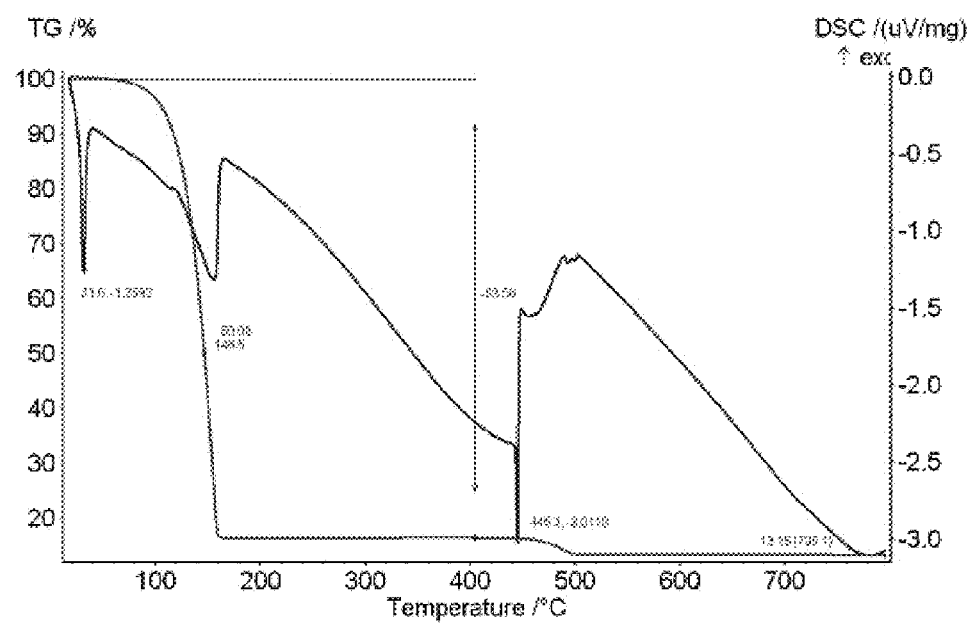
FIG. 6 is a simultaneous thermographic analysis plot of STA TG/DSC data for Te$_2$(t-Bu)$_2$.

FIG. 6 is a simultaneous thermal analysis (STA) plot of thermogravimetry (TG) and differential scanning calorimetry (DSC) data for $Te_2(t-Bu)_2$.

In general, the alkyl moieties of the dialkyl ditelluride compounds of the invention can be of any suitable type, e.g., $C_1$-$C_8$ alkyl substituents. Examples include methyl, ethyl, isopropyl, and t-butyl. Preferably, such alkyl substituents include tertiary carbon moieties. Tertiary butyl or tertiary carbons in general are preferred as having high radical stability.

Illustrative examples of dialkyl ditelluride compounds of the invention include dimethyl ditelluride, diethyl ditelluride, diisopropyl ditelluride, and di-tertiary-butyl ditelluride.

Other ditelluride compounds contemplated by the invention can utilize other ligands, such as $C_1$-$C_{12}$ hydrocarbyl (aryl, fluoroalkyl, allyl, alkenyl, dienyl), or silyl or substituted silyl ligands.

The above-described tellurium precursor compounds of the invention can be used for chemical vapor deposition and/or atomic layer deposition, to form tellurium or tellurium-containing films on substrates, e.g., semiconductor wafers or other microelectronic device base structures. Such precursor compounds when present in solid phase can be delivered by solid delivery techniques, wherein the solid precursor is contained in a precursor storage and vapor delivery vessel, which is subjected to heating to volatilize the solid precursor, e.g., by sublimation, so that the precursor vapor can be discharged selectively from the vessel, as needed in the downstream deposition process.

The precursor when present in solid phase may also be dissolved in solvent medium, as described above, and delivered by liquid delivery techniques to a vaporizer, for volatilization to form a precursor vapor that then is contacted under a vapor deposition conditions with a wafer or other suitable substrate. When present in liquid phase, the tellurium precursor can be delivered by liquid delivery techniques from a suitable precursor storage vessel. Bubbler techniques may also be employed.

The specific delivery technique employed in the practice of the invention utilizing such Te(II) and Te(IV) compounds can be selected based on the process conditions needed for delivery for contacting with the substrate on which Te or Te-containing films are to be formed. In general, it is desired to carry out deposition by CVD and/or ALD techniques at temperatures below 400° C.

The deposition of tellurium species in accordance with the invention can be carried out to form GST phase change memory devices, or other tellurium-based microelectronic device structures.

The features and advantages of the invention are more fully shown by the following non-limiting examples.

Example 1

Synthesis of Te[N(SiMe$_3$)$_2$]$_2$ 4.78 g (12.53 mmol) of TeI$_e$ are suspended in 100 mL of THF in a 200 mL Schlenk flask equipped with a magnetic stirring bar. A solution of 5.00 g (25.06 mmol) of K[N(SiMe$_3$)$_2$] in 50 mL of THF is prepared in a 100 mL Schlenk flask. The K[N(SiMe$_3$)$_2$] solution is added to the TeI$_e$ suspension via cannula at 0° C. (with ice-bath cooling). The reaction mixture turns yellow immediately and then brown after ca. 10 minutes. It is stirred another hour at 0° C. and then at ambient temperature overnight. The volatiles are removed in vacuum and the remaining dark brown solid is extracted with 100 mL of n-pentane. It is filtered through a medium glass-filter frit resulting in an orange solution. The pentane is removed in vacuum leaving 4.41 g of the crude product behind as an orange solid. The solid is sublimed at 200 mTorr and an oil bath temperature of 100° C. for two hours, affording 3.37 g (7.51 mmol; 60% yield) of analytical pure product as a yellow, crystalline solid.

Figure 7:
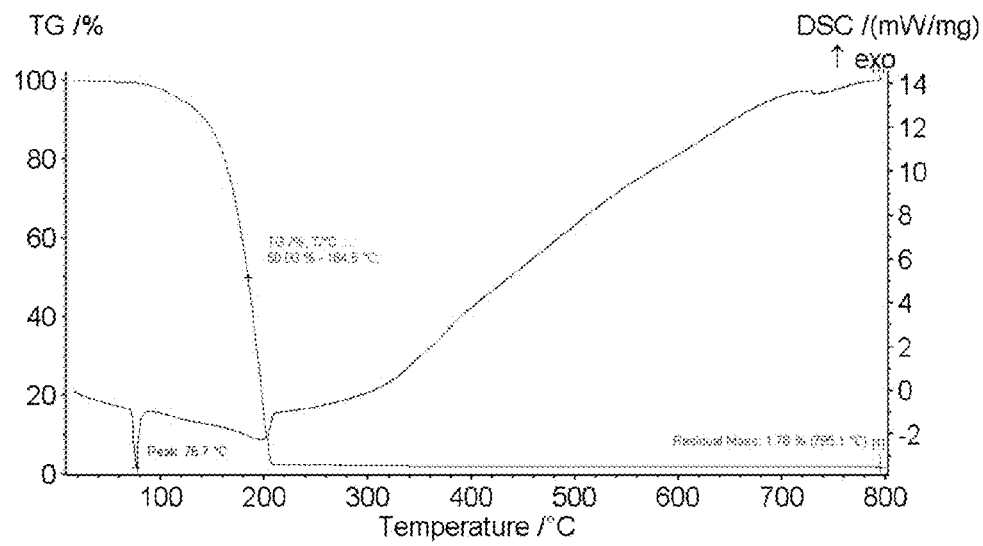
FIG. 7 is a STA of Te[N(SiMe$_3$)$_2$]$_2$.

The product yielded by the foregoing procedure had the following characteristics: 1H NMR in $C_6D_6$, ppm: 0.338 (s, 18H, SiMe$_3$); melting point: 66° C. FIG. 7 is a STA plot of the Te[N(SiMe$_3$)$_2$]$_2$ product.

Example 2

Synthesis of NHTeCl$_2$ 5.00 g (18.56 mmol) of TeCl$_4$ are suspended in 400 mL of THF (only partially soluble) in a 500 mL Schlenk flask equipped with a magnetic stirring bar. A solution of 6.40 g (37.12 mmol) of N,N'-di-tert-butylethylenediamine and 7.51 g (74.24 mmol) of triethylamine in 10 mL of THF is prepared. This solution in added to the TeCl$_4$ suspension and the reaction mixture turns cloudy immediately. A mild exothermic reaction is observed. The reaction mixture is stirred overnight a room temperature, and then filtered through a medium glass-filter frit, leading to yellow solution. The volatiles are removed in a vacuum leaving 5.96 g (16.20 mmol; 87.1% yield) of analytically pure product behind as a pale yellow, microcrystalline solid.

X-ray analysis quality crystals were obtained by dissolving 0.5 g of product in 6 mL of toluene in a sample vial inside a controlled atmosphere glove-box. The solution is filtered through a PTFE syringe filter and then placed in a −25° C. freezer. After 16 hours large, pale yellow, plate like crystals of the title compound were obtained, which were suitable for X-ray analysis.

The compound can be further purified by sublimation. In a typical experiment a sublimation device is charged with 5 g of material and the material is sublimed at 200 mTorr pressure and an oil bath temperature of 70° C. for two hours. Typical yields of the sublimation vary between 80-90%. The product yielded by the foregoing procedure had the following characteristics: 1H NMR in $C_6D_6$, ppm: 3.133 (s, 4H, N—CH$_2$—CH$_2$—N); 1.189 (s, 18H, N-t-Bu).

Example 3

Figure 8:
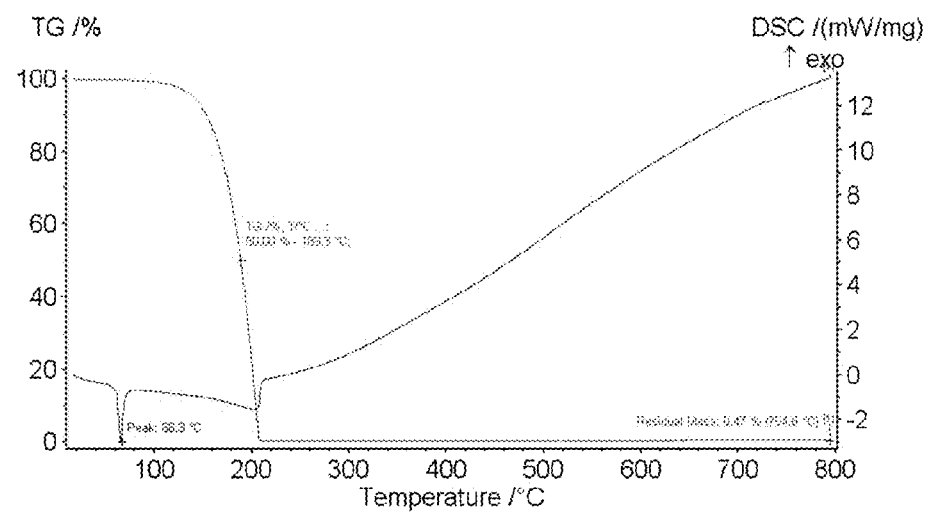
FIG. 8 is a STA of Te[N(SiMe$_3$)(t-Bu)]$_2$

Synthesis of Te[N(SiMe$_3$)(t-Bu)]$_2$ 3.00 g of (7.87 mmol) TeI$_2$ are suspended in 100 mL of diethyl ether in a 200 mL Schlenk flask equipped with a magnetic stirring bar. A solution of 2.38 g (15.73 mmol) of Li[N(SiMe$_3$)(t-Bu)] in 50 mL of diethyl ether is prepared in a 100 mL Schlenk flask. The Li[N(SiMe$_3$)(t-Bu)] solution is added to the TeI$_2$ suspension via cannula at 0° C. (ice-bath cooling). It is stirred another hour at 0° C. and then at ambient temperature overnight. The volatiles are removed in vacuum and the remaining dark brown solid is extracted with 150 mL of n-pentane and filtered through a medium glass-filter frit, resulting in an orange solution. The pentane is removed in vacuum leaving 2.60 g (6.25 mmol; 79.5%) of analytically pure product behind as a yellow-orange solid. The compound can be further purified by sublimation at 200 mTorr and an oil bath temperature of 100° C. for two hours, affording 2.05 g (4.93 mmol; 63% yield) of product as a yellow, crystalline solid. The product yielded by the foregoing procedure had the following characteristics: 1H NMR in $C_6D_6$, ppm: 1.400 (s, 9H, t-Bu); 0.399 (s, 9H, SiMe$_3$); melting point: 77° C. FIG. 8 is a STA plot of the Te[N(SiMe$_3$)(t-Bu)]$_2$ product.

Example 4

Synthesis of N,N'-di-tert-butyl-2,3-dimethylethylenediamide telluriumdichloride 2.36 g (8.79 mmol) of TeCl$_4$ are suspended in 100 mL of THF (only partially soluble) in a 200 mL Schlenk flask equipped with a magnetic stirring bar. A solution of 1.77 g (8.79 mmol) of N,N'-di-tert-butyl-2,3-dimethylethylenediamine and 1.78 g (17.58 mmol) of triethylamine in 5 mL of THF is prepared. This solution in added to the TeCl$_4$ suspension and the reaction mixture turns cloudy immediately. A mild exothermic reaction is observed. It is stirred overnight a room temperature. The reaction mixture is filtered through a medium glass-filter frit leading to an amber colored solution. The volatiles are removed in a vacuum leaving 1.93 g (4.85 mmol; 55% yield) of analytically pure product behind as an amber colored, microcrystalline solid.

X-ray analysis quality crystals were obtained by dissolving 0.5 g of product in 5 mL of toluene in a sample vial inside a controlled atmosphere glove-box. The solution is filtered through a PTFE syringe filter and then placed in a −25° C. freezer. After 32 hours pale yellow crystals of the title compound were obtained, that were suitable for X-ray analysis. The product yielded by the foregoing procedure had the following characteristics: 1H NMR in C$_6$D$_6$, ppm: 2.722 (q, 2H, N(Me)-CH—CH-(Me)N); 1.227 (s, 18H, N-t-Bu); 1.080 (s, 3H, N(Me)-CH—CH-(Me)N); 1.059 (s, 3H, N(Me)-CH—CH-(Me)N).

Example 5

Di-tert-butyltelluride and Ge[Pr$^i$NC(n-Bu)NPr$^i$]$_2$, wherein Pr$^i$ is isopropyl, were utilized as respective tellurium and germanium precursors to form a GeTe film. GeTe films can be formed using this germanium precursor, denoted GeBAMDN or GeM for ease of notation, and di-tert-butyltelluride, at temperatures below 300° C. or lower, e.g., below 280° C. or even 260° C. or lower. In general, lower temperatures will result in lower content of tellurium, but the specific deposition rate of the film will also depend on the germanium and tellurium delivery rates in the deposition system.

Di-tert-butyltelluride and Ge[Pr$^i$NC(n-Bu)NPr$^i$]$_2$ were used to deposit GeTe films at the illustrative conditions identified below, with the following film thickness and tellurium concentration results.

| Sample | Temperature, pressure, Film Growth Duration | Flow rates of GeM and Te(tBu)$_2$ | Film Thickness, % Te in film |
|---|---|---|---|
| 1 | 280° C., 8 torr, 8 min | 20/160 GeM/Te(tBu) 2 μmole/min | 124 Å, 7.3% Te |
| 2 | 260° C., 8 torr, 16 min | 20/160 GeM/Te(tBu) 2 μmole/min | 179 Å, 12.5% Te |

The invention in another aspect involves use of control agents to combat vapor phase pre-reaction of the precursors described herein, that otherwise causes uneven nucleation on the substrate, longer incubation times for deposition reactions, and lower quality product films. Such pre-reaction may for example be particularly problematic in applications involving chalcogenide films, related source materials (O, S, Se, Te, Ge, Sb, Bi, etc.), and/or manufacture of phase change memory and thermoelectric devices.

Pre-reaction may occur when the precursor reagents described herein are introduced to the deposition chamber, as in chemical vapor deposition, and may also occur in atomic layer deposition (ALD) processes, depending on the specific arrangement of ALD cycle steps and the specific reagents involved.

The invention therefore contemplates the use of control agents with the precursors described herein, whereby detrimental gas phase pre-reactions are suppressed, mitigated or eliminated, so that deposition reactions are induced/enhanced on the substrate surface, and films of superior character are efficiently formed.

The control agents that can be utilized with precursors of the invention for such purpose include agents selected from the group consisting of (i) heteroatom (O, N, S) organo Lewis base compounds, (ii) free radical inhibitors, and (iii) deuterium-containing reagents.

These agents can be utilized to lessen deleterious gas phase pre-reaction I'll precursors by various approaches, including:

(1) addition to the precursor composition of a pre-reaction suppressant comprising one or more heteroatom (O, N, S) organo Lewis base compounds such as 1,4-dioxane, thioxane, ethers, polyethers, triethylamine (TEA), triazine, diamines, N,N,N',N'-tetramethylethylenediamine, N,N,N'-trimethylethylenediamine, amines, imines, and pyridine;

(2) addition to the precursor composition of a free radical inhibitor, such as butylated hydroxy toluene (BHT), hydroquinone, butylated hydro anisole (BHA), diphenylamine, ethyl vanillin, etc.;

(3) use of modified chalcogenide precursors, in which hydrogen substituents have been replaced with deuterium (D) substituents, to provide deuterated analogs for vapor phase deposition; and (4) addition to the precursor composition of a deuterium source, to deuterate the precursor in situ.

The pre-reaction-combating agents described above (suppressants, free radical inhibitors, deuterium sources and/or deuterated precursors) can be introduced to any of the feed streams to the vapor deposition process in which the film is to be formed. For example, such pre-reaction-combating agents can be introduced to one or more of precursor feed stream(s), inert carrier gas stream(s) to which chalcogenide precursor(s) or other reagents are subsequently added for flow to the deposition chamber, co-reactant feed stream(s) flowed to the deposition chamber, and/or any other stream(s) that is/are flowed to the deposition chamber and in which the pre-reaction-combating agent(s) is/are useful for reduction or elimination of premature reaction of the precursors that would otherwise occur in the absence of such agent(s).

The aforementioned suppressants, free radical inhibitors and/or deuterium source reagents in specific embodiments are co-injected with the precursor(s), e.g., metal source reagent(s), to effect at least partial reduction of pre-reaction involving the precursor(s) and reagent(s).

The pre-reaction-combating agent can alternatively be added directed to the deposition locus, e.g., the deposition chamber to which the precursor vapor is introduced for contacting with the substrate to deposit the film thereon, to suppress deleterious vapor phase pre-reaction involving the precursor(s) and/or other reagents.

As another approach, in the broad practice of the present invention, the suppressant, free radical inhibitor and/or deuterium source can be added to a solution containing the precursor and/or another metal source reagent, and the resulting solution can be utilized for liquid delivery processing, in which the solution is flowed to a vaporizer to form a source vapor for contacting with the substrate to deposit the deposition species thereon.

Alternatively, if the precursor and/or another metal source reagent are not in an existing solution, the suppressant, free radical inhibitor and/or deuterium source can be added to form a mixture or a solution with the precursor and/or another metal source reagent, depending on the respective phases of the materials involved, and their compatibility/solubility.

As a still further approach, the suppressant, free radical inhibitor and/or deuterium source can be utilized for surface treatment of the substrate prior to contacting of the substrate with the precursor and/or other metal source reagent.

The invention therefore contemplates various vapor deposition compositions and processes for forming films on substrates, in which pre-reaction of the precursors is at least partially attenuated by one or more pre-reaction-combating agents selected from among heteroatom (O, N, S) organo Lewis base compounds, sometimes herein referred to as suppressor agents, free radical inhibitors, and/or deuterium source reagents. Use of previously synthesized deuterated precursors or organometal compounds is also contemplated, as an alternative to in situ deuteration with a deuterium source. By suppressing precursor prereaction with these approaches, product films of superior character can be efficiently formed.

The control agent can be used for combating pre-reaction of chalcogenide precursor in a process in which multiple feed streams are flowed to a deposition locus to form a film on a substrate, wherein at least one of the multiple feed streams includes a precursor susceptible to pre-reaction adversely affecting the film, in which the method involves introducing the control agent to at least one of such multiple feed streams or supplied materials therefor, or to the deposition locus.

The pre-reaction combating reagent alternatively can be introduced to passivate the surface of a growing chalcogenide film or slow the deposition rate, followed by reactivation using an alternative precursor or co-reactant (for example $H_2$, $NH_3$, plasma, $H_2O$, hydrogen sulfide, hydrogen selenide, diorganotellurides, diorganosulfides, diorganoselenides, etc.), thereby carrying out passivation/retardation followed by reactivation steps, e.g., as an alternating repetitive sequence. Such sequence of passivation/retardation followed by reactivation can be carried out for as many repetitive cycles as desired, in ALD or ALD-like processes. The steps may be carried out for the entire deposition operation, or during some initial, intermediate or final portion thereof.

The invention therefore contemplates precursor compositions including the precursor and the pre-reaction-combating reagent. Within the categories of pre-reaction-combating reagents previously described, viz., (i) heteroatom (O, N, S) organo Lewis base compounds, (ii) free radical inhibitors, and (iii) deuterium-containing reagents, suitable pre-reaction-combating reagents for specific applications may be readily determined within the skill of the art, based on the disclosure herein.

Heteroatom (O, N, S) organo Lewis base compounds may be of varied type, e.g., containing an oxo (—O—) moiety, a nitrogen ring atom or pendant amino or amide substituent, a sulfur ring atom or pendant sulfide, sulfonate or thio group, as effective to at least partially lessen pre-reaction of the precursor and other organo metal reagents in the process system. Illustrative examples of heteroatom (O, N, S) organo Lewis base compounds having utility in specific applications of the invention include, without limitation, 1,4-dioxane, thioxane, ethers, polyethers, triethylamine, triazine, diamines, N,N,N',N'-tetramethylethylenediamine, N,N,N'-trimethylethylenediamine, amines, imines, pyridine, and the like.

The heteroatom organo Lewis base compound in various specific embodiments of the invention may include a guanidinate compound, e.g., $(Me_2N)_2C=NH$.

One preferred class of heteroatom organo Lewis base compounds for such purpose includes $R_3N$, $R_2NH$, $RNH_2$, $R_2N(CH_2)_xNR_2$, $R_2NH(CH_2)_xNR_2$, $R_2N(CR_2)_xNR_2$, and cyclic amines $—N(CH_2)_x—$, imidazole, thiophene, pyrrole, thiazole, urea, oxazine, pyran, furan, indole, triazole, triazine, thiazoline, oxazole, dithiane, trithiane, crown ethers, 1,4,7-triazacyclononane, 1,5,9-triazacyclododecane, cyclen, succinamide, and substituted derivatives of the foregoing, wherein R can be hydrogen or any suitable organo moieties, e.g., hydrogen, $C_1$-$C_8$ alkyl, $C_1$-$C_8$ alkoxy, $C_1$-$C_8$ alkene, $C_1$-$C_8$ alkyne, and $C_1$-$C_8$ carboxyl, and wherein x is an integer having a value of from 1 to 6.

The heteroatom organo Lewis base compounds may be utilized in the precursor composition at any suitable concentration, as may be empirically determined by successive deposition runs in which the heteroatom organo Lewis base compound concentration is varied, and character of the resulting film is assessed, to determine an appropriate concentration. In various embodiments, the heteroatom organo Lewis base compound may be utilized in the concentration of 1-300% of the amount of precursor. Specific sub-ranges of concentration values within a range of 0.01-3 equivalents of the heteroatom organo Lewis base compound may be established for specific classes of precursors, without undue experimentation, based on the disclosure herein.

The pre-reaction-combating reagent may additionally or alternatively comprise free radical inhibitors that are effective to lessen the extent of pre-reaction between the precursor and another organo metal reagent. Such free radical inhibitors may be of any suitable type, and may for example include hindered phenols. Illustrative free radical inhibitors include, without limitation, free radical scavengers selected from the group consisting of: 2,6-ditert-butyl-4-methyl phenol, 2,2,6,6-tetramethyl-1-piperidinyloxy, 2,6-dimethylphenol, 2-tert-butyl-4-hydroxyanisole, 3-tert-butyl-4-hydroxyanisole, propyl ester 3,4,5-trihydroxy-benzoic acid, 2-(1,1-dimethylethyl)-1,4 benzenediol, diphenylpicrylhydrazyl, 4-tert-butylcatechol, N-methylaniline, 2,6-dimethylaniline, p-methoxydiphenylamine, diphenylamine, N,N'-diphenyl-p-phenylenediamine, p-hydroxydiphenylamine, phenol, octadecyl-3-(3,5-di-tert-butyl-4-hydroxyphenyl)propionate, tetrakis(methylene (3,5-di-tert-butyl-4-hydroxy-hydrocinnamate)methane, phenothiazines, alkylamidonoisoureas, thiodiethylene bis(3,5-di-tert-butyl-4-hydroxy-hydrocinnamate, 1,2-bis(3,5-di-tert-butyl-4-hydroxyhydrocinnamoyl)hydrazine, tris(2-methyl-4-hydroxy-5-tert-butylphenyl)butane, cyclic neopentanetetrayl bis (octadecyl phosphite), 4,4'-thiobis(6-tert-butyl-m-cresol, 2,2'-methylenebis(6-tert-butyl-p-cresol), oxalyl bis(benzylidenehydrazide) and mixtures thereof. Preferred free radical inhibitors include BHT, BHA, diphenylamine, ethyl vanillin, and the like.

Useful concentrations of the free radical inhibitor may be in a range of from 0.001 to about 0.10% by weight of the weight of the precursor, in various specific embodiments. More generally, any suitable amount of free radical inhibitor may be employed that is effective to combat the pre-reaction of the precursor in the delivery and deposition operations involved in the film formation process.

The deuterium source compounds afford another approach to suppressing pre-reaction of the chalcogenide precursor. Such deuterium source compounds may be of any suitable type, and may for example include deuterated pyridine, deuterated pyrimidine, deuterated indole, deuterated imidazole, deuterated amine and amide compounds, deuterated alkyl reagents, etc., as well as deuterated analogs of the precursors that would otherwise be used as containing hydrogen or protonic substituents.

Deuterides that may be useful in the general practice of invention as pre-reaction-combating reagents include, without limitation, germanium and antimony compounds of the formulae $R_xGeD_{4-x}$ and $R_xSbD_{3-x}$ wherein R can be hydrogen or any suitable organo moieties, e.g., hydrogen, $C_1$-$C_8$ alkyl, $C_1$-$C_8$ alkoxy, $C_1$-$C_8$ alkene, $C_1$-$C_8$ alkyne, and $C_1$-$C_8$ carboxyl, and wherein x is an integer having a value of from 1 to 6.

The deuterium source reagent may be utilized at any suitable concentration that is effective to combat pre-reaction of the precursor. Illustrative deuterium source reagent concentrations in specific embodiments of the invention can be in a range of 0.01 to about 5% by weight, based on the weight of precursor.

Thus, a deuterium source compound may be added to one or more of the feed streams to the vapor deposition process, and/or one of the precursors or other feed stream components may be deuterated in the first instance.

The concentrations of the pre-reaction-combating agents utilized in the practice of the present invention to at least partially eliminate pre-reaction of the precursors can be widely varied in the general practice of the present invention, depending on the temperatures, pressures, flow rates and specific compositions involved. The above-described ranges of concentration of the pre-reaction-combating reagents of the invention therefore are to be appreciated as being of an illustrative character only, with applicable concentrations being readily determinable within the skill of the art, based on the disclosure herein.

The specific mode of introduction or addition of the pre-reaction-combating agent to one or more of the feed streams to the deposition process may correspondingly be varied, and may for example employ mass flow controllers, flow control valves, metering injectors, or other flow control or modulating components in the flow circuitry joining the source of the pre-reaction-combating agent with the streams being flowed to the deposition process during normal film-forming operation. The process system may additionally include analyzers, monitors, controllers, instrumentation, etc., as may be necessary or appropriate to a given implementation of the invention.

In lieu of introduction or addition of the pre-reaction-combating agent to one or more of the flow streams to the vapor deposition process, the pre-reaction-combating agent may be mixed with precursor in the first instance, as a starting reagent material for the process. For example, the pre-reaction-combating agent may be mixed in liquid solution with the precursor, for liquid delivery of the resulting precursor solution to a vaporizer employed to generate precursor vapor for contact with the substrate to deposit the film thereon.

As mentioned, the pre-reaction-combating agent may be added to the deposition locus to provide active gas-phase suppression of pre-reaction of the precursor vapor(s) that would otherwise be susceptible to such deleterious interaction.

As a still further alternative, the pre-reaction-combating agent may be used as a preliminary surface treatment following which the precursor and co-reactants (e.g., $H_2$, $NH_3$, plasma, $H_2O$, hydrogen sulfide, hydrogen selenide, diorganotellurides, diorganosulfides, diorganoselenides, etc.) are delivered to the substrate surface to effect deposition on such surface. For such purpose, the pre-reaction-combating agent may be introduced into one of more of the flow lines to the deposition process and flow to the substrate in the deposition process chamber, prior to initiation of flow of any precursors. After the requisite period of contacting of the substrate with such pre-reaction-combating agent has been completed, the flow of the pre-reaction-combating agent can be terminated, and normal feeding of flow streams to the deposition chamber can be initiated.

It will be apparent from the foregoing description that the pre-reaction-combating agent may be introduced in any of a wide variety of ways to effect diminution of the pre-reaction of the precursor in the deposition system.

In one embodiment of the invention, a vapor phase deposition system is contemplated, comprising:

a vapor deposition chamber adapted to hold at least one substrate for deposition of a film thereon;

chemical reagent supply vessels containing reagents for forming the film;

first flow circuitry arranged to deliver said reagents from said chemical reagent supply vessels to the vapor deposition chamber;

a pre-reaction-combating agent supply vessel containing a pre-reaction-combating agent;

second flow circuitry arranged to deliver the pre-reaction-combating agent from the pre-reaction-combating agent supply vessel to the first flow circuitry, to said chemical reagent supply vessels and/or to the vapor deposition chamber.

Figure 9:
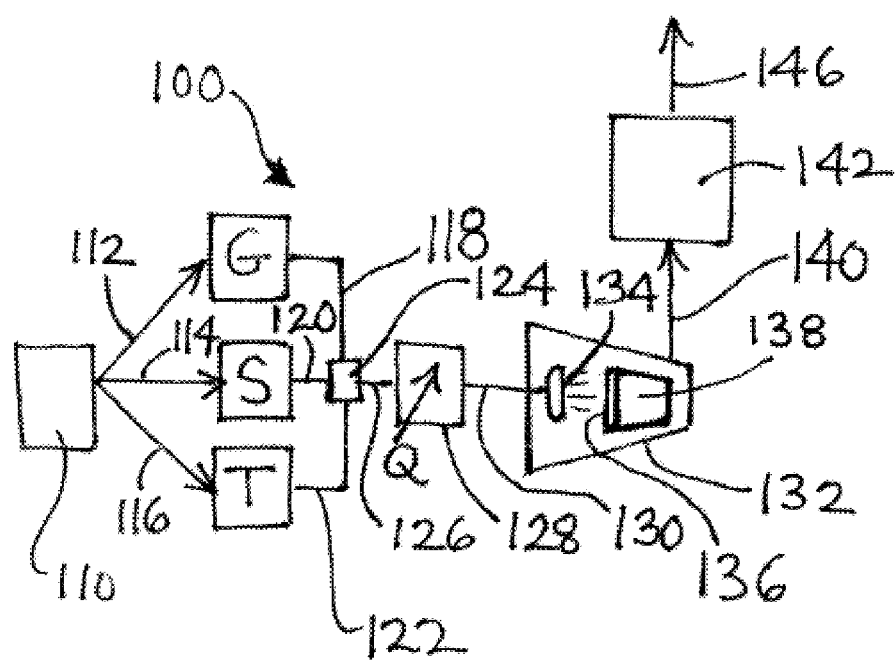
FIG. 9 is a schematic representation of a vapor deposition system according to one embodiment of the present invention, wherein suppression of pre-reaction of the precursors is achieved by addition of pre-reaction-combating reagent to one or more feed streams in the vapor deposition system.

FIG. 9 is a schematic representation of a vapor deposition system 100 in one embodiment thereof.

In this illustrative system, a pre-reaction-combating agent is contained in a supply vessel 110. The pre-reaction-combating agent can comprise a pre-reaction suppressant, a free radical inhibitor, a deuterium source, or a combination of two or more of such agents and/or types of such agents.

The pre-reaction-combating agent supply vessel is joined by respective flow lines 112, 114 and 116, to germanium, antimony and tellurium reagent supply vessels, labeled "G," "S" and "T," respectively. The germanium precursor in vessel "G" may be a tetraalkyl or tetraamido germanium compound, such as tetramethyl germanium, tetraethyl germanium, tetraallyl germanium, tetrakis(dimethylamino)germane or other organo germanium compounds. Furthermore, precursor "G" may be a germylene compound wherein the lone pair on Ge(II) can react in the gas-phase with chalcogen precursors in the absence of a pre-reaction suppressant. The antimony precursor in vessel "S" can be a trialkyl or triamido antimony compound, such as tributyl antimony, triisopropyl antimony, tris(dimethylamino)antimony or other organo antimony compound. The tellurium precursor in vessel "T" can be a dialkyl or diamido tellurium compound, such as diisopropyl tellurium, dibutyl tellurium, bis[bis(trimethylsilyl)amino]tellurium or other organo tellurium compound.

The pre-reaction-combating agent therefore can be added to any of the germanium, antimony and/or tellurium precursors in the respective "G," "S" and "T" vessels, via the corresponding flow line(s), which for such purpose may have flow control valves or other flow-modulating components therein.

In the specific process embodiment shown, the germanium, antimony and tellurium precursors are flowed in liquid form in feed lines 118, 120 and 122, respectively, to the mixing chamber 124, and the resulting precursor mixture then is flowed from the mixing chamber 124 in line 126 to vaporizer 128. In the vaporizer, the liquid precursor mixture and pre-reaction-combating agent are volatilized to form a precursor vapor. The precursor vapor then flows in line 130 to the showerhead disperser 134 in vapor deposition chamber 132, for discharge of precursor mixture onto the wafer substrate 136 mounted on susceptor 138 in the deposition chamber.

The precursor vapor contacting the wafer substrate 136 serves to deposit the germanium, antimony and tellurium metals on the substrate, to form a thin film of germanium-antimony-tellurium (GST) material, e.g., for manufacture of a phase change random access memory device.

The contacted precursor vapor, depleted in metals content, is discharged from the vapor deposition chamber 132 in line 140, and flows to the effluent abatement unit 142. In the effluent abatement unit 142, the discharged effluent vapor is treated, e.g., by scrubbing, catalytic oxidation, electrochemical treatment, or in other manner, to yield a final effluent that is discharged from the abatement unit in line 146.

It will be appreciated that these schematic representation of the vapor deposition system shown in FIG. 9 is of an illustrative character, and that numerous other arrangements could be utilized for deployment and use of the pre-reaction-combating agent, including those previously illustratively discussed herein. For example, the pre-reaction-combating agent could be introduced directly to the mixing chamber 124, for blending therein with the respective GST precursors. Alternatively, the pre-reaction-combating agent could be introduced into manifold 118, or other mixing chamber, blender, etc., for combination with the precursor that is being transported to the deposition locus.

The system shown in FIG. 9 employs liquid delivery of the respective precursors. It will be recognized that if solid-phased precursors are employed, then solid delivery techniques may be employed, in which solid precursor is volatilized, e.g., by sublimation of the solid starting material.

In lieu of using a deuterating agent as the pre-reaction-combating agent in the FIG. 9 system, one or more of the germanium, antimony and tellurium precursors could be supplied in the first instance as a deuterated analog of an organo germanium, antimony or tellurium precursor, in which hydrogen substituents of the organo moiety have been replaced with deuterium.

The pre-reaction-combating reagents may be employed in the broad practice of the present invention to produce improved films for the manufacture of semiconductor products. In general, the pre-reaction-combating reagents described herein may be utilized in various combinations in specific applications, to suppress or eliminate pre-reaction of the precursor(s) and provide superior nucleation and final film properties.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A method of forming a phase change material comprising a tellurium-containing film, comprising volatilizing a tellurium precursor composition to form a tellurium precursor vapor, and contacting the tellurium precursor vapor with a substrate to deposit tellurium thereon, wherein the tellurium precursor composition comprises a tellurium precursor comprising a diorgano ditelluride compound wherein each organo group is the same and is selected from the group consisting of $C_1$-$C_8$ alkyl; $C_1$-$C_{12}$ hydrocarbyl selected from aryl, fluoroalkyl, allyl, alkenyl or dienyl; silyl; and substituted silyl.

2. The method of claim 1, wherein the tellurium precursor is a dialkyl ditelluride wherein the alkyl is $C_1$-$C_8$ alkyl.

3. The method of claim 1, wherein the tellurium precursor is a $C_1$-$C_{12}$ hydrocarbyl selected from aryl, fluoroalkyl, allyl, alkenyl or dienyl.

4. The method of claim 1, wherein the tellurium precursor is diisopropyl ditelluride.

5. The method of claim 1, wherein the tellurium precursor is dimethyl ditelluride.

6. The method of claim 1, wherein the tellurium precursor is diethylditelluride.

7. The method of claim 1, wherein the phase change material is a GST film.

8. The method of claim 1, wherein the contacting comprises atomic layer deposition.

9. The method of claim 1, wherein the contacting comprises chemical vapor deposition.

10. The method of claim 1, wherein the tellurium-containing film is an amorphous $Sb_2Te_3$ film.

11. The method of claim 1, wherein the tellurium is deposited at a temperature below 300° C.

12. The method of claim 1, wherein the tellurium precursor composition further comprises a solvent medium with the tellurium precursor dissolved therein.

13. A method of forming a GST film comprising volatilizing a tellurium precursor composition to form a tellurium precursor vapor, and contacting the tellurium precursor vapor with a substrate to deposit tellurium thereon, wherein the tellurium precursor composition comprises a tellurium precursor comprising a diorgano ditelluride compound wherein each organo group is the same and is selected from the group consisting of $C_1$-$C_8$ alkyl; $C_1$-$C_{12}$ hydrocarbyl selected from aryl, fluoroalkyl, allyl, alkenyl or dienyl; silyl; and substituted silyl.

14. The method of claim 13, wherein the tellurium precursor is a dialkyl ditelluride wherein the alkyl is $C_1$-$C_8$ alkyl.

15. The method of claim 14, wherein the tellurium precursor is dimethyl ditelluride, diethyl ditelluride or diisopropyl ditelluride.

16. The method of claim 15, wherein the tellurium precursor is diisopropyl ditelluride.

17. The method of claim 13, wherein the contacting comprises atomic layer deposition.

18. The method of claim 13, wherein the contacting comprises chemical vapor deposition.

19. The method of claim 13, wherein the tellurium-containing film is an amorphous $Sb_2Te_3$ film.

20. The method of claim 13, wherein the tellurium is deposited at a temperature below 300° C.

* * * * *